(12) United States Patent
Kim et al.

(10) Patent No.: US 7,060,470 B2
(45) Date of Patent: Jun. 13, 2006

(54) **ISOFLAVONE-β-D-GLUCAN PRODUCED BY *AGARICUS BLAZEI* IN THE SUBMERGED LIQUID CULTURE AND METHOD OF PRODUCING SAME**

(75) Inventors: Jeong Ok Kim, Gyeongsangnam-do (KR); Yeong Lae Ha, Gyeongsangnam-do (KR); Young Suk Kim, Gyeongsangnam-do (KR); Cherl Woo Park, Gyeongsangnam-do (KR)

(73) Assignee: HK Biotech Co., Ltd., Gyeongsangnam-Do (KR)

( * ) Notice: Subject to any disclaimer, the term of this patent is extended or adjusted under 35 U.S.C. 154(b) by 38 days.

(21) Appl. No.: 10/890,537

(22) Filed: Jul. 12, 2004

(65) Prior Publication Data

US 2005/0069989 A1 Mar. 31, 2005

(30) Foreign Application Priority Data

Sep. 29, 2003 (KR) ...................... 10-2003-0067439

(51) Int. Cl.
*C12P 19/04* (2006.01)
*C12N 9/42* (2006.01)
*C12N 1/14* (2006.01)
*C07H 17/07* (2006.01)
*C07H 1/00* (2006.01)
*C07D 311/74* (2006.01)

(52) U.S. Cl. .................. 435/101; 435/209; 435/254.1; 536/8; 536/123.12; 549/403

(58) Field of Classification Search ............... 435/101, 435/209, 254.1; 536/8, 123.12; 549/403
See application file for complete search history.

(56) References Cited

U.S. PATENT DOCUMENTS

2003/0064484 A1* 4/2003 Horiuchi et al. ............ 435/101

OTHER PUBLICATIONS

"Enhanced anticarcinoginicity of submerged liquid culture of *Agaricus blazei* murill"; Authors: Young Suk Kim; Division of Applied Life Science, Graduate School Gyeongsang, National University, Jinju 660-701, Korea; 108 Pages; Aug. 2003 and its English Translation; 64 Pages.

* cited by examiner

*Primary Examiner*—Robert A. Wax
*Assistant Examiner*—Rosanne Kosson
(74) *Attorney, Agent, or Firm*—Cantor & Colburn LLP

(57) ABSTRACT

The present invention relates to low and medium molecular weight isoflavone-β-D-glucan produced by submerged liquid culture of *Agaricus blazei*, a method of producing the isoflavone-β-D-glucan using autolysis enzyme of *Agaricus blazei* mycelia, and use of the isoflavone-β-D-glucan for anti-cancer and immunoenhancing effect.

7 Claims, 16 Drawing Sheets

Tube #25 + 80EP

Tube #25

Tube #35 + 80EP

Tube #35

Tube #65 + 80EP

Tube #65

Tube #83 + β-glucan

Tube #83

ISOFLAVONE-β-D-GLUCAN PRODUCED BY *AGARICUS BLAZEI* IN THE SUBMERGED LIQUID CULTURE AND METHOD OF PRODUCING SAME

TECHNICAL FIELD

The present invention relates to low and medium molecular weight isoflavone-β-D-glucan produced by submerged liquid culture of *Agaricus blazei*, a method of producing the isoflavone-β-D-glucan using autolysis enzyme of *Agaricus blazei* mycelia, and use of the isoflavone-β-D-glucan for anti-cancer and immunoenhancing effect.

BACKGROUND ART

Cancer holds the most fatal disease in the statistics of mortality, so that anti-cancer agents have been a matter of continued concern. Conventional anti-cancer agents have much toxicity to affect normal cells since they are lack of specificity to cancer cells, which results in a variety adverse effects such as depilation, lowering of immunity and liver function, etc.

Considering the above, various researches have been carried out to obtain natural anti-cancer agents from all sorts of food having no or little adverse effect. As a result, it is revealed that β-D-glucan obtained from mushroom mycelia and isoflavone contained in soybean, etc. have anti-cancer effect.

β-D-glucan is a main bioactive component in mushroom. It is found that the anti-cancer activity of mushroom derives from the activation of immunocyte by β-D-glucan to delay the progress of cancer and to prevent the transition of cancer. Accordingly, β-D-glucan may be used along with cancer treatment to improve the effect.

β-D-glucan, extract from mycelium culture of mushroom, is produced on a commercial scale in some advanced countries. For example, AHCC, which is imported from Japan, is produced by mixing extracts from mycelium cultures of seven mushrooms and is distributed through sales network for hospital to cancer patients. Further, arabinoxylan, which is extract from *Lentinus edodes* mycelia, is distributed in the US. In Korea, extract of *Phellinus linteus* mycelia, which is produced on a commercial scale by the trade name of Mesima-EX (HAN KOOK SIN YAK Corp, Korea), is on the clinical test.

The extracts of mushroom mycelium culture commercialized by this time have not been distributed on a large scale since the extraction process costs very high. The amount of extract of mushroom mycelium culture, that is, the amount of polysaccharides depends on the cultivation period of mushroom and the growth rate of mycelia. In general, the cultivation period of *Lentinus edodes, Phellinus linteus, Ganoderma lucidum*, etc. is long and the growth of mycelia is slow, which limits the amount of extracts.

The polysaccharides extracted from mycelium culture require to be hydrolyzed to medium or low molecular weight polysaccharides in order to be absorbed easily in the body. However, the enzyme for the hydrolyzation is hard to obtain, which makes the cost high. Further, the method of separating and purifying the medium or low molecular weight polysaccharides produced from the hydrolyzation has technical difficulty, so that the yield is very low.

Isoflavone, contained mainly in soybean, exists as aglycon form (e.g., daidzein, genistein or glycitein), as glycoside form thereof (e.g., daidzin, genistin or glycitin), as acetylglycoside thereof (e.g., acetylglucose), or as malonylglycoside thereof (e.g., malonylglucose). It is found that isoflavone has anti-mutagenic and anti-cancer effect. The anti-cancer effect of isoflavone is mainly caused by genistein in the aglycon form, and the glycoside form is not known to have anti-cancer effect.

Considering the above, efforts have continued for the development of an anti-cancer agent with immunoenhancing effect, without affecting adversely on normal cell, and a method of preparing the agent in great quantities with low cost.

DISCLOSURE OF THE INVENTION

It is an object of the present invention to provide a glycoside of isoflavone and β-D-glucan having anti-cancer effect and immunoenhancing effect, and a method of producing the glycoside from mushroom mycelium culture.

In accordance with one aspect of the present invention, it is provided a method of producing isoflavone-β-D-glucan, which comprises the steps of:

culturing *Agaricus blazei* mycelia in a liquid medium containing isoflavone to produce a high molecular weight isoflavone-β-D-glucan;

separating the high molecular weight isoflavone-β-D-glucan from the liquid culture of *Agaricus blazei* mycelia;

separating an autolysis enzyme from a separate liquid culture of *Agaricus blazei* mycelia;

adding the autolysis enzyme to the high molecular weight isoflavone-β-D-glucan to produce a low and medium molecular weight isoflavone-β-D-glucan; and separating and purifying the low and medium molecular weight isoflavone-β-D-glucan.

Preferably, the step of separating the high molecular weight isoflavone-β-D-glucan from the liquid culture of *Agaricus blazei* mycelia comprises:

extracting the liquid culture of *Agaricus blazei* mycelia with boiling water and concentrating the extract;

adding ethanol to the concentrated extract to make precipitation; and separating the precipitate.

In the above step of separating the high molecular weight isoflavone-β-D-glucan from the liquid culture of *Agaricus blazei* mycelia, ethanol is preferably added in the concentration of 80%.

Preferably, the step of separating an autolysis enzyme from a separate liquid culture of *Agaricus blazei* mycelia comprises:

filtrating the liquid culture of *Agaricus blazei* mycelia under reduced pressure;

adding trichloroacetic acid to the filtered liquid culture of *Agaricus blazei* mycelia to make precipitation; and separating the precipitate.

In the above step of producing a low and medium molecular weight isoflavone-β-D-glucan, the autolysis enzyme is preferably added to the high molecular weight isoflavone-β-D-glucan at pH 4.5~5.5.

In accordance with another aspect of the present invention, it is provided a method of producing isoflavone-β-D-glucan, which comprises the steps of:

culturing *Agaricus blazei* mycelia in a liquid medium containing isoflavone to produce a high molecular weight isoflavone-β-D-glucan;

activating an autolysis enzyme in the liquid culture of *Agaricus blazei* mycelia to produce a low and medium molecular weight isoflavone-β-D-glucan; and separating and purifying the low and medium molecular weight isoflavone-β-D-glucan.

Preferably, the step of activating an autolysis enzyme from the liquid culture of *Agaricus blazei* mycelia is carried out by adjusting the pH of culture medium to pH 4.5~5.5 for 1~3 hours.

In accordance with still another aspect of the present invention, it is provided a low and medium molecular weight isoflavone-β-D-glucan produced by the above-mentioned method.

The low and medium molecular weight isoflavone-β-D-glucan produced from a liquid culture of *Agaricus blazei* mycelia is used as anti-cancer and immunoenhancing agent.

Generally, polysaccharides having anti-cancer activity have been obtained from Basidiomycetes by extracting fruit body or mycelium cultured in solid medium or liquid medium. In solid culture, a long period of time is required for culturing and the process of extracting the anti-cancer polysaccharides is difficult. Further, the amount of polysaccharides extracted from fruit body is very low, and therefore, it is difficult to produce them on a large scale. On the other hand, in liquid culture, a short period of time is required, and it is possible to culture in a settled condition, which enables mycelia including a regular content of polysaccharides to be obtained on a large scale at low cost.

The present invention is characterized in using *Agaricus blazei* mycelia as the mushroom mycelia cultured in liquid media containing isoflavone to produce low and medium molecular weight isoflavone-β-D-glucan.

According to the present invention, low and medium molecular weight isoflavone-β-D-glucan is prepared from high molecular weight isoflavone-β-D-glucan extracted from liquid culture of *Agaricus blazei* mycelia, in order to enhance internal absorption thereof. In the present invention, autolysis enzyme secreted by *Agaricus blazei* mycelia is used to digest the high molecular weight isoflavone-β-D-glucan at an optimum condition for the activity of the enzyme. Especially, *Agaricus blazei* mycelium is selected for its highest activity of autolysis enzyme.

Low and medium molecular weight isoflavone-β-D-glucan produced according to the present invention may be used for anti-cancer and immunoenhancing effect. The isoflavone-β-D-glucan of the present invention is very effective in killing cancer cells and shows no toxic effect on normal cells. It is found that isoflavone in free form has anti-cancer effect. However, the anti-cancer effect of isoflavone-β-D-glucan as glycoside has never been found before the present invention.

Low and medium molecular weight isoflavone-β-D-glucan produced according to the present invention is characterized to have anti-cancer effect as well as immunoenhancing effect. The anti-cancer effect of the low and medium molecular weight isoflavone-β-D-glucan is remarkably increased with immunoenhancing effect.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Hereinafter, the present invention will be described in detail, in conjunction with various examples. These examples are provided only for illustrative purposes, and the present invention is not to be construed as being limited to these examples.

First of all, a mushroom strain having highest activity of autolysis enzyme was selected. In an experiment for determining the activity of autolysis enzyme by measuring the change of viscosity in the liquid culture medium of *Agaricus blazei* (AB), *Pleurotus ostreatus* (PO), *Coprinus comatus* (CC), *Lentinus edodes* (LE), *Phellinus linteus* (PL) and *Ganoderma lucidum* (GL), *Agaricus blazei* (AB) was confirmed to have the highest activity.

Figure 1:
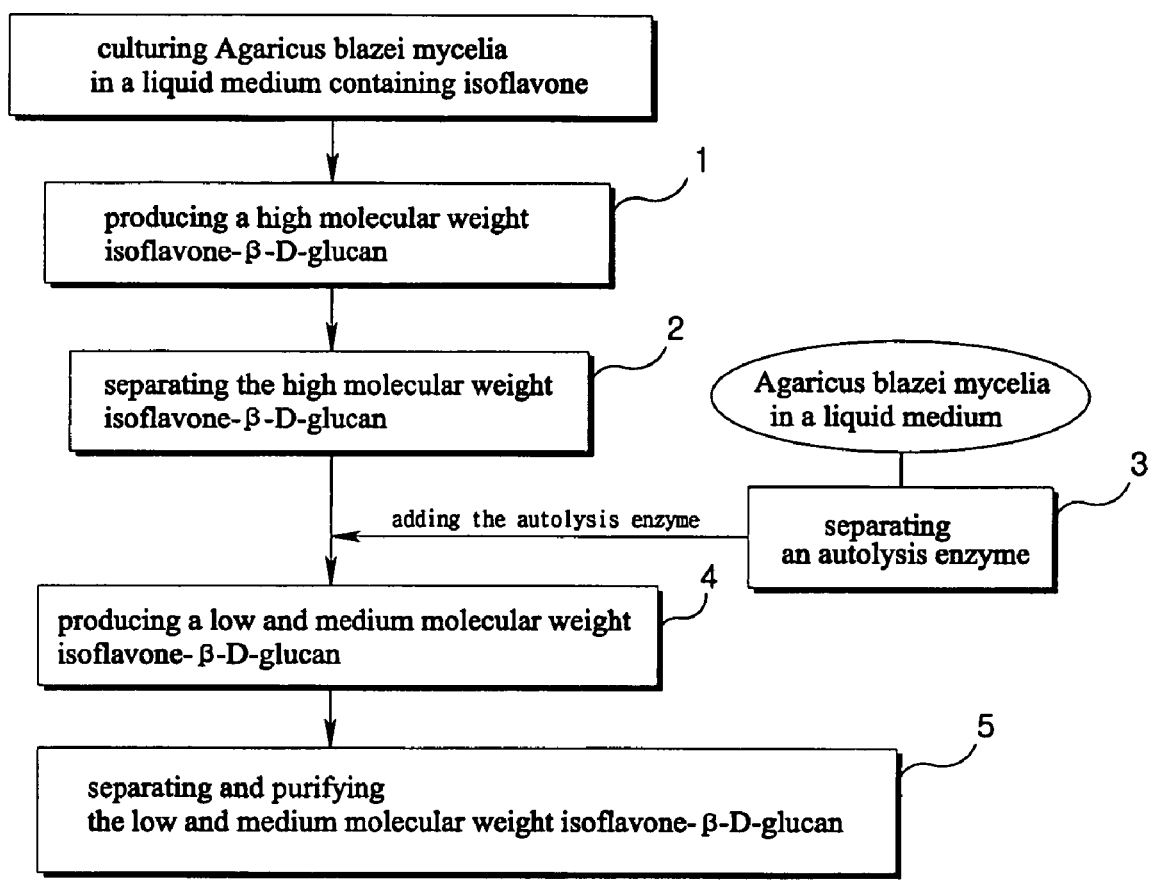
FIG. 1 shows a process of preparing a low and medium molecular weight isoflavone-β-D-glucan according to the present invention.

FIG. 1 shows a process of preparing a low and medium molecular weight isoflavone-β-D-glucan according to the present invention. As shown in FIG. 1, the process comprises step (1) of producing high molecular weight isoflavone-β-D-glucan by culturing AB mycelia in a liquid medium containing isoflavone.

In the next step (2), the high molecular weight isoflavone-β-D-glucan is separated from the liquid culture of AB mycelia by extracting the liquid culture with boiling water, concentrating the extract, adding ethanol to the concentrated extract to make precipitation and separating the precipitate. In the process of treating the extract with ethanol, 80% ethanol has the maximum effect on obtaining high molecular weight isoflavone-β-D-glucan.

Further, the process of preparing a low and medium molecular weight isoflavone-β-D-glucan according to the present invention comprises step (3) of separating autolysis enzyme from a separate liquid culture of AB mycelia.

The next process of preparing isoflavone-β-D-glucan is step (4) of adding the autolysis enzyme obtained from the liquid culture of AB mycelia to the high molecular weight isoflavone-β-D-glucan to produce a low and medium molecular weight isoflavone-β-D-glucan.

The autolysis enzyme has the best activity in the condition of pH 4.5 to 5.5 and at the temperature of 53° C. for 1 to 3 hours. Considering the viscosity of product, the reaction for 3 hours appeared to be optimum. However, the effect of reaction time on producing low and medium molecular weight isoflavone-β-D-glucan had no difference between 3 hours and 1 hour. Accordingly, the reaction is preferable to be carried out for 1 hour.

The process of preparing isoflavone-β-D-glucan according to the present invention further comprises step (5) of separating and purifying the low and medium molecular weight isoflavone-β-D-glucan. The low and medium molecular weight isoflavone-β-D-glucan is separated by DEAE column chromatography. The separated fraction is concentrated by vacuum concentrator and then separated by silica gel column chromatography.

Figure 12:
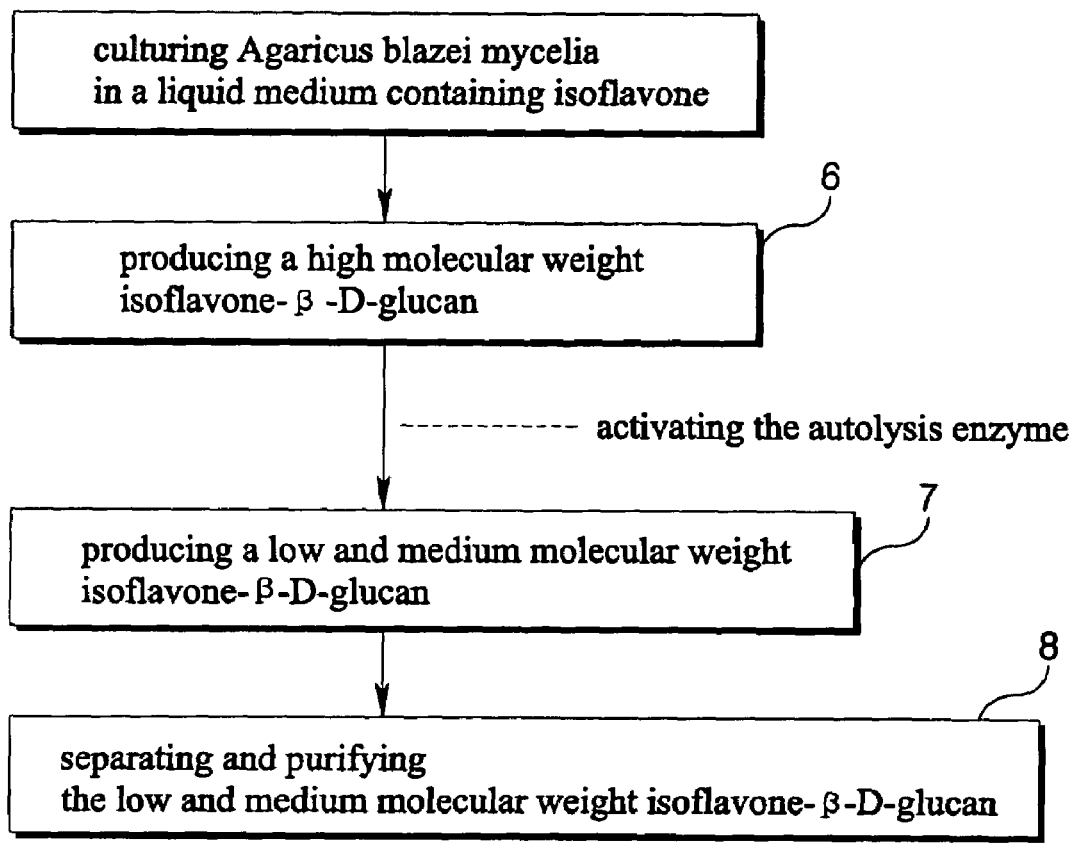
FIG. 12 shows another process of preparing a low and medium molecular weight isoflavone-β-D-glucan according to the present invention.

FIG. 12 shows another process of preparing a low and medium molecular weight isoflavone-β-D-glucan according to the present invention. In FIG. 12, steps 6 and 8 are carried out by the same procedure of steps 1 and 5 in FIG. 1. However, step 7 in FIG. 12 are carried out by adjusting the pH of culture medium to 4.5~5.5 for 1~3 hours instead of treating the high molecular weight isoflavone-β-D-glucan with separated autolysis enzyme.

PREPARATIVE EXAMPLE

Selection of Mushroom Strain for the Production of Autolysis Enzyme

*Agaricus blazei* (AB), *Pleurotus ostreatus* (PO), *Coprinus comatus* (CC), *Lentinus edodes* (LE), *Phellinus linteus* (PL) and *Ganoderma lucidum* (GL) were cultured in liquid culture medium at 25° C. for three days in the condition of 1 v/v/m aeration. Liquid culture of each strain (10 ml) and polysaccharides prepared from the liquid culture were added with 80% ethanol (80EP). The mixtures were then incubated at 53° C. and 63° C. for five hours. Degree of autolysis was determined by measuring the change of viscosity of 80EP before and after the reaction. The following Table 1 shows the change of viscosity.

TABLE 1

| Mushroom strains | Viscosity (ml/sec) | | |
|---|---|---|---|
| | 0 hr | After 5 hrs | Δvis/hr |
| AB | 18,850 | 1,500 | 3,470 |
| PO | 1,250 | 650 | 120 |
| CC | 1,310 | 790 | 104 |
| LE | 1,120 | 970 | 30 |
| PL | 1,570 | 1,100 | 90 |
| GL | 1,750 | 1,210 | 108 |

As shown in Table 1, AB has the highest value of 3,470 ml/sec in the change of viscosity (Δviscosity/hour). PO and CC also have rather higher values of 120 and 104 ml/sec. As a result, it is considered that AB has the highest degree of autolysis compared to other strains.

EXAMPLE 1

Production and Separation of High Molecular Weight Isoflavone-β-D-Glucan

The culture medium contained soybean powder or natural source including soybean powder. Natural isoflavone separated from soybean or synthetic isoflavone may also be used. The liquid medium were added with brown sugar as carbon source and inorganic salts, and then autoclaved at 120° C. for 30 minutes.

AB mycelia were inoculated in the liquid culture medium containing isoflavone and cultured with aeration or stirring for 1 to 7 days to produce high molecular weight isoflavone-β-D-glucan. The molecular weight of the high molecular weight isoflavone-β-D-glucan was at least 30,000.

Liquid culture of AB mycelia was extracted with boiling water at 100° C. for 10 hours, and the extract was autoclaved at 121° C. for 1 hour.

The extract of liquid culture of AB mycelia was treated with 80% ethanol to make precipitation and then centrifuged to remove supernatant. The precipitate was separated to obtain high molecular weight isoflavone with β-D-glucan having the molecular weight of at least 100,000.

EXAMPLE 2

Selection of Ethanol Fraction Having the Highest Content of High Molecular Weight Isoflavone-β-D-Glucan The extract of liquid culture of AB mycelia was suspended in ethanol to prepare 10 to 80% ethanol solution to induce precipitation. Each precipitate was separated and then applied to Biosep S-2000 column.

Figure 2:
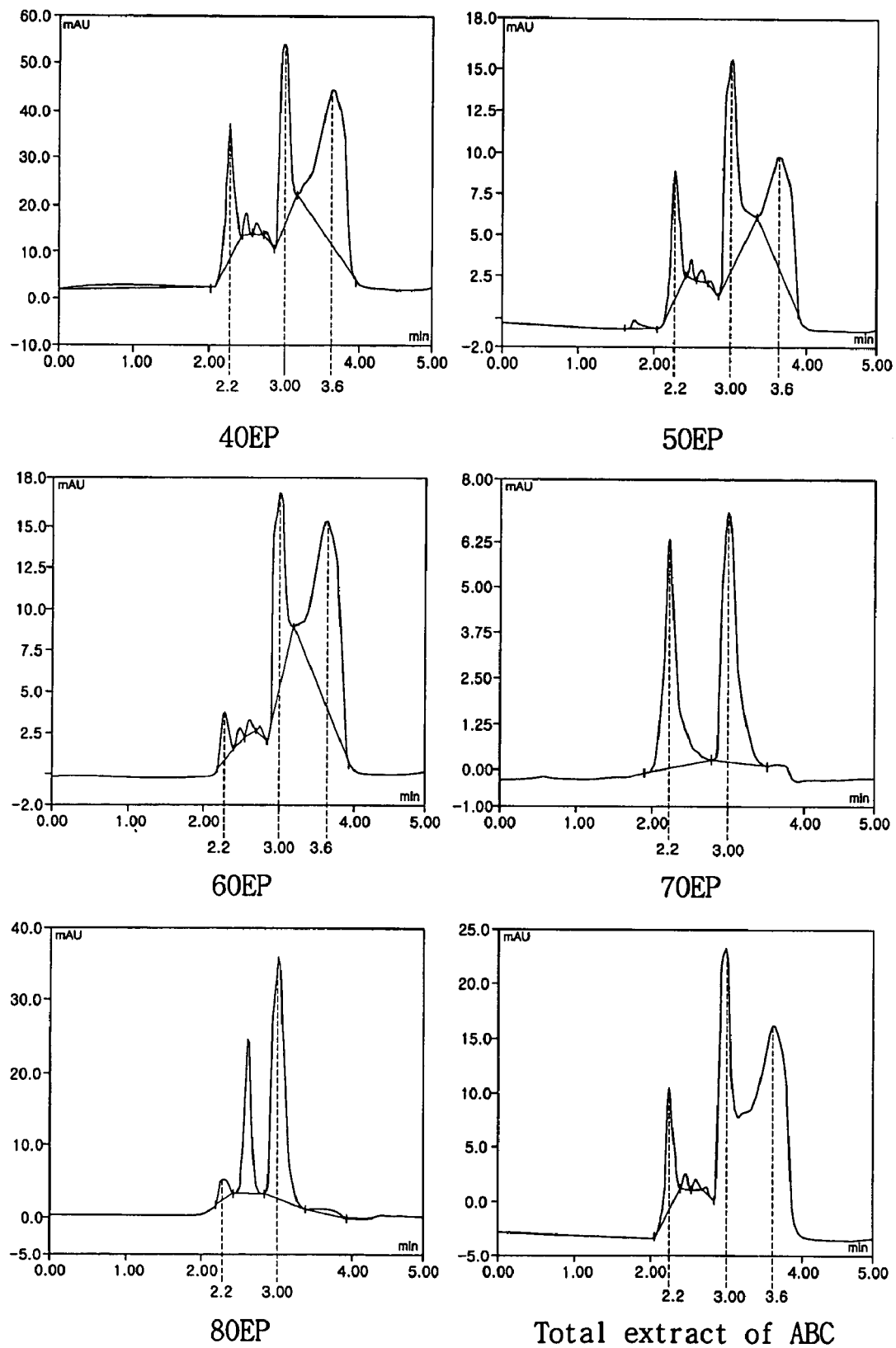
FIG. 2 is HPLC chromatograms of the extract of liquid culture of *Agaricus blazei* mycelia treated with various concentrations of ethanol solution.

FIG. 2 is HPLC chromatograms of the extract of liquid culture of *Agaricus blazei* mycelia treated with various concentrations of ethanol solution (40, 50, 60, 70 and 80% ethanol) and then separated with Biosep S-2000 column. The chromatogram on the right side below represents the chromatogram of total extract of liquid culture of AB mycelia. In FIG. 2, horizontal axis represents time (minutes) and vertical axis represents length (mAU).

As shown in FIG. 2, the high molecular weight isoflavone-β-D-glucan, obtained by treating 80% ethanol to the liquid culture of AB mycelia to induce precipitation, hereinafter referred to '80 EP (80% ethanol precipitate)', shows similar chromatograph pattern to 70 EP, both showing peaks at RT (retention time) 2.2 and 3. In 80 EP, the peak at RT 3 is higher than the peak at RT 2.2, while two peaks at RT 3 and 2.2 have similar heights to those of 70 EP. Other fractions have similar patterns to the total extract of liquid culture of AB mycelia, showing peaks at RT 2.2, 3 and 3.6.

From the above, it is considered that 80 EP has higher amount of high molecular weight isoflavone-β-D-glucan than other ethanol precipitates have. Further, 80 EP does not have unnecessary peaks, such as the peak at RT 3.6 which is found in other EP. Accordingly, 80 EP is used to increase the yield of isoflavone-β-D-glucan according to the present invention.

EXAMPLE 3

Separation and Fractionation of Autolysis Enzyme

The separation of autolysis enzyme was carried out by filtratng the liquid culture of AB mycelia at reduced pressure. TCA (trichloroacetic acid) was added to the filtrate to the concentration of 10% and the mixture was placed at 4° C. for 24 hours. The resultant was centrifuged at 4° C. and 10,000 rpm for 15 minutes to obtain the precipitate.

The precipitate was further fractionated by DEAE (diethylaminoethyl) column chromatography and each fraction was determined its UV absorbance at 280 nm.

Figure 3:
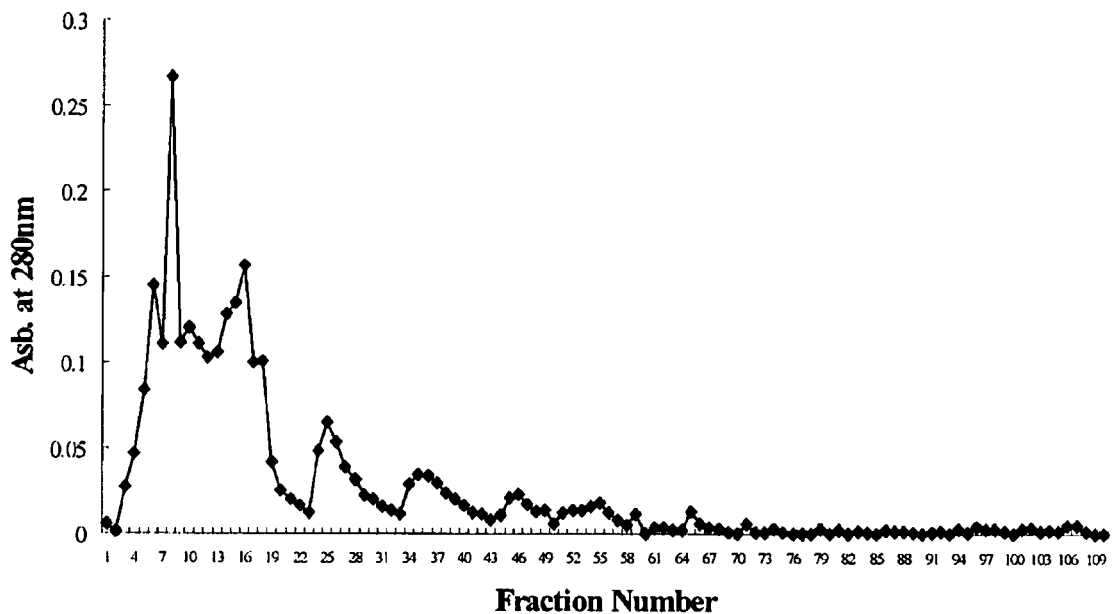
FIG. 3 shows fractionation of the precipitate of the liquid culture of *Agaricus blazei* mycelia by DEAE column chromatography.

FIG. 3 shows fractionation of the precipitate of the liquid culture of *Agaricus blazei* mycelia by DEAE column chromatography. In FIG. 3, horizontal axis represents number of each fraction and vertical axis represents UV absorbance at 280 nm. As shown in FIG. 3, UV absorbance of each fraction was monitored and eight fractions were obtained showing UV absorbance at 280 nm. Fraction #2 (tube #8) showed the maximum UV absorbance. When autolysis activity of each fraction was tested, tube #8 showed the highest activity. Accordingly, tube #8 was used for treating the 80 EP obtained in Example 2 to prepare low and medium molecular weight isoflavone-β-D-glucan.

Figure 4:
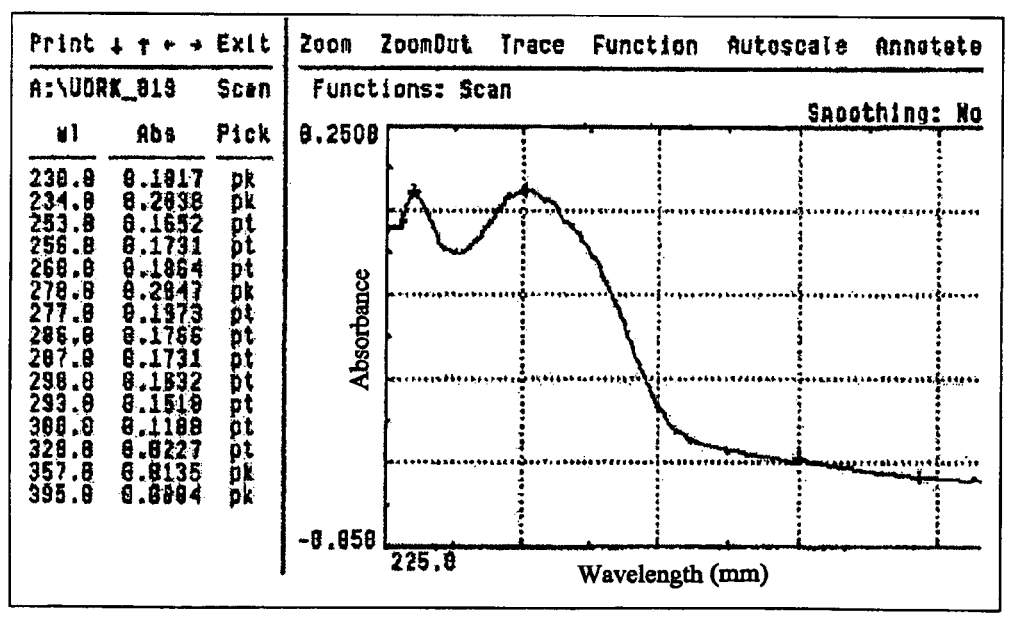
FIG. 4 is UV spectrum of DEAE column fraction #2 (tube #8) at 225~445 nm.

FIG. 4 is UV spectrum of DEAE column fraction #2 (tube #8) at 225~445 nm. In FIG. 4, horizontal axis represents wavelength, vertical axis represents absorbance, and the left box shows the numerical value of wavelength and absorbance. As shown in FIG. 4, fraction #2 (tube #8) has the maximum UV absorbance at 270 nm.

EXAMPLE 4

Determination of Autolysis Enzyme Activity

The fraction of DEAE column chromatography was added to 80 EP obtained in Example 2. The production of low and medium molecular weight isoflavone-β-D-glucan from high molecular weight isoflavone-β-D-glucan was confirmed by using TSK column and C18 column. In TSK column chromatography, $H_2O$ was used as mobile phase at 1 ml/min. In C18 column chromatography, MeOH:1 mM ammonium acetate (6:4) was used as mobile phase at 1 ml/min. Isoflavone was identified at UV 257 nm and 267 nm. RI detector was used to identify β-D-glucan.

EXAMPLE 5

Determination of Molecular Weight of Autolysis Enzyme

As tube #8 obtained in Example 3 showed maximum autolysis activity, molecular weight of the protein contained in tube #8 was determined by SDS-PAGE (sodium dodecyl sulfate-polyacrylamide gel electrophoresis).

The fraction of tube #8 was dried and then SDS-PAGE sample buffer was added to dissolve the resultant. Electrophoresis was performed on 12% SDS-PAGE according to Laemmli. Size markers used were β-galactosidase (175 kDa), paramyosin (83 kDa), glutamic dehydrogenase (62 kDa), aldolase (48 kDa), triosephosphate isomerase (33 kDa), β-lactoglobulin A (25 kDa), lysozyme (17 kDa) and aprotinin (7 kDa)

Figure 5:
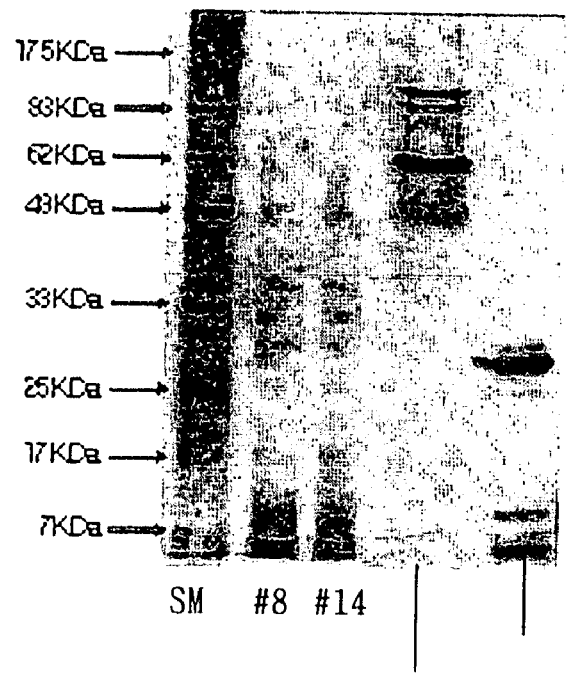
FIG. 5 shows SDS-PAGE pattern of tubes #8 and #14.

FIG. 5 shows SDS-PAGE pattern of tubes #8 and #14. In FIG. 5, SM of horizontal axis is size marker and vertical axis represents molecular weight of the protein used as size marker. As shown in FIG. 5, molecular weight of the protein in tube #8 corresponds to 7 kDa, which shows that molecular weight of autolysis enzyme is about 7 kDa.

EXAMPLE 6

Production of Low and Medium Molecular Weight Isoflavone-β-D-Glucan by Autolysis Enzyme After adjusting its pH to 5.5, the high molecular weight isoflavone-β-D-glucan obtained by treating 80% ethanol to the liquid culture of AB mycelia (80 EP) was added with 10 ml of autolysis enzyme separated from DEAE column in Example 3. The mixture was placed at 53° C. for 1 hours to produce a low and medium molecular weight isoflavone-β-D-glucan. The molecular weight of obtained isoflavone-β-D-glucan was less than about 30,000.

In order to determine the optimum condition for the activity of autolysis enzyme obtained from the liquid culture of AB mycelia, the liquid culture of AB mycelia and 80 EP were reacted at each conditions of pH 4.5, 5.5, 6.5 and 7.5 and temperature of 53° C. and 63° C. for 1, 3, 5, 15 and 24 hours and the viscosity was measured in each condition.

Table 2 shows the viscosity of liquid culture of AB mycelia reacted with autolysis enzyme. As shown in Table 2, the autolysis enzyme obtained from AB mycelia has maximum activity at the condition of pH 4.5 to 5.5 and the temperature of 53° C. for 3 hours of reaction.

TABLE 2

| Reaction time | 53° C. | | | | 63° C. | | | |
|---|---|---|---|---|---|---|---|---|
| | pH 4.5 | pH 5.5 | pH 6.5 | pH 7.5 | pH 4.5 | pH 5.5 | pH 6.5 | pH 7.5 |
| 0 | 18,750 | 18,850 | 19,300 | 19,750 | 18,750 | 18,850 | 19,300 | 19,750 |
| 1 hr | 16,250 | 16,950 | 17,700 | 16,500 | 17,250 | 15,750 | 18,250 | 16,650 |
| 3 hrs | 1,500 | 1,500 | 12,500 | 2,300 | 7,750 | 15,500 | 16,000 | 16,500 |
| 5 hrs | 1,500 | 1,650 | 6,000 | 2,050 | 1,550 | 3,650 | 4,300 | 4,200 |
| 15 hrs | 1,650 | 1,500 | 1,650 | 1,550 | 1,550 | 1,500 | 1,900 | 1,700 |
| 24 hrs | 1,650 | 1,650 | 1,500 | 1,600 | 1,500 | 1,750 | 1,750 | 1,750 |

As shown in Table 2, the viscosity of liquid culture of AB mycelia decreased from 18,750 to 1,500 after the reaction for 3 hours at the condition of pH 4.5 and 53° C. As a result, it is found that the autolysis enzyme has maximum activity at the condition of pH 4.5 to 5.5 and the temperature of 53° C. for 3 hours of reaction

EXAMPLE 7

Identification of Low and Medium Molecular Weight Isoflavone-β-D-Glucan

Low and medium molecular weight isoflavone-β-D-glucan was identified by TLC and HPLC.

(1) Identification by TLC (Thin-Layer Chromatography)

Free sugars or polymeric sugar has no UV absorbance. Therefore, in order to examine that an area separated by TLC has the material having UV absorbance, sugars, or sugars having UV absorbance, the separated band was detected with UV lamp and also analyzed by color development with diphenylamine aridine phosphate (DAP).

The fraction separated by silica gel column chromatography was developed by TLC (Silica gel 60F-254 plate, 5×10 cm). The mobile phase was butanol:ethanol:$H_2O$ (5:3:3) (v/v/v). The separated band was treated by DAP and UV lamp was used to identify the material having UV absorbance.

Figure 6:
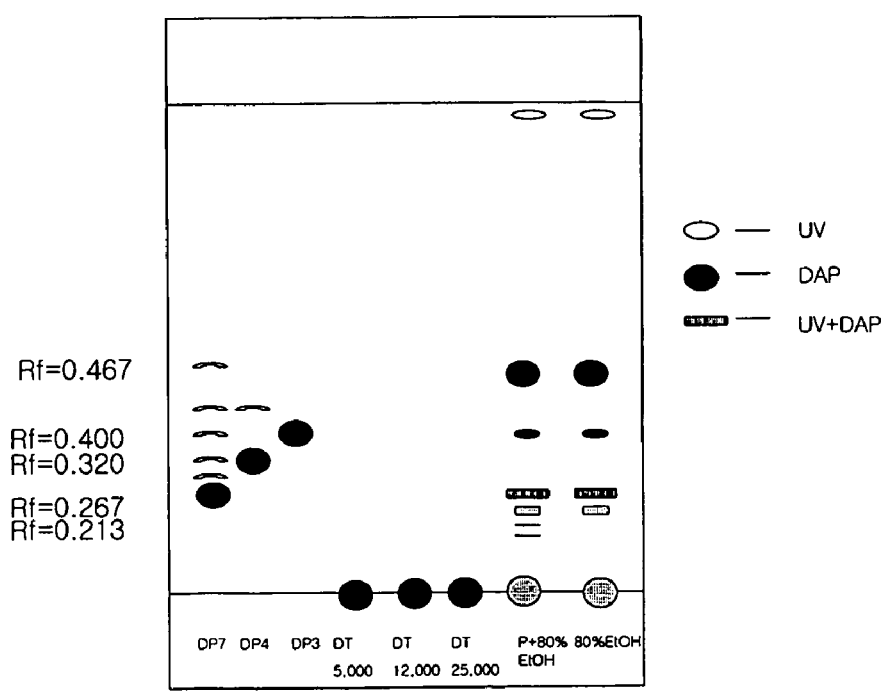
FIG. 6 shows TLC pattern of 80 EP reacted with autolysis enzyme.

FIG. 6 shows TLC pattern of 80 EP reacted with autolysis enzyme. In horizontal axis of FIG. 6, DP7 represents maltoheptose; DP4, maltotetrose; DP3, maltotriose; DT 5,000, dextran 5,000; DT 12,000, dextran 12000; DT 25,000, dextran 25,000; P+80% ethanol, 80 EP treated with autolysis enzyme; and 80% ethanol, 80 EP without treatment with autolysis enzyme. The vertical axis of FIG. 6 represents Rf value which means the separation of material.

As shown in FIG. 6, low molecular weight polysaccharides (DP7 or less) move, while medium or higher molecular weight polysaccharides (MW 5,000) do not moved. In high molecular weight polysaccharides treated with autolysis enzyme, low molecular weight sugars (DP3 or less) showing color development by DAP are mixed with the materials having UV absorbance and showing color development by DAP. Especially, medium or higher molecular weight polysaccharides showing no movement have UV absorbance, and sugars of DP7 also have UV absorbance. Further, the materials having UV absorbance only are also included herein.

The above results show that high molecular weight polysaccharides are converted to medium and low molecular weight materials by autolysis and that the medium and low molecular weight materials are combined with the materials having UC absorbance.

(2) Separation by HPLC (High Performance Liquid Chromatography)

Bio-Sep S2000 column (mobile phase; 20 mM sodium phosphate), TSK column (mobile phase; $H_2O$) and C18 column (mobile phase; MeOH:1 mM ammonium acetate (6:4)) were used. Flow rate was 1 ml/min in all cases. UV detector (UV 257 nm, 267 nm, 280 nm) and RI detector was used.

Figure 7A:
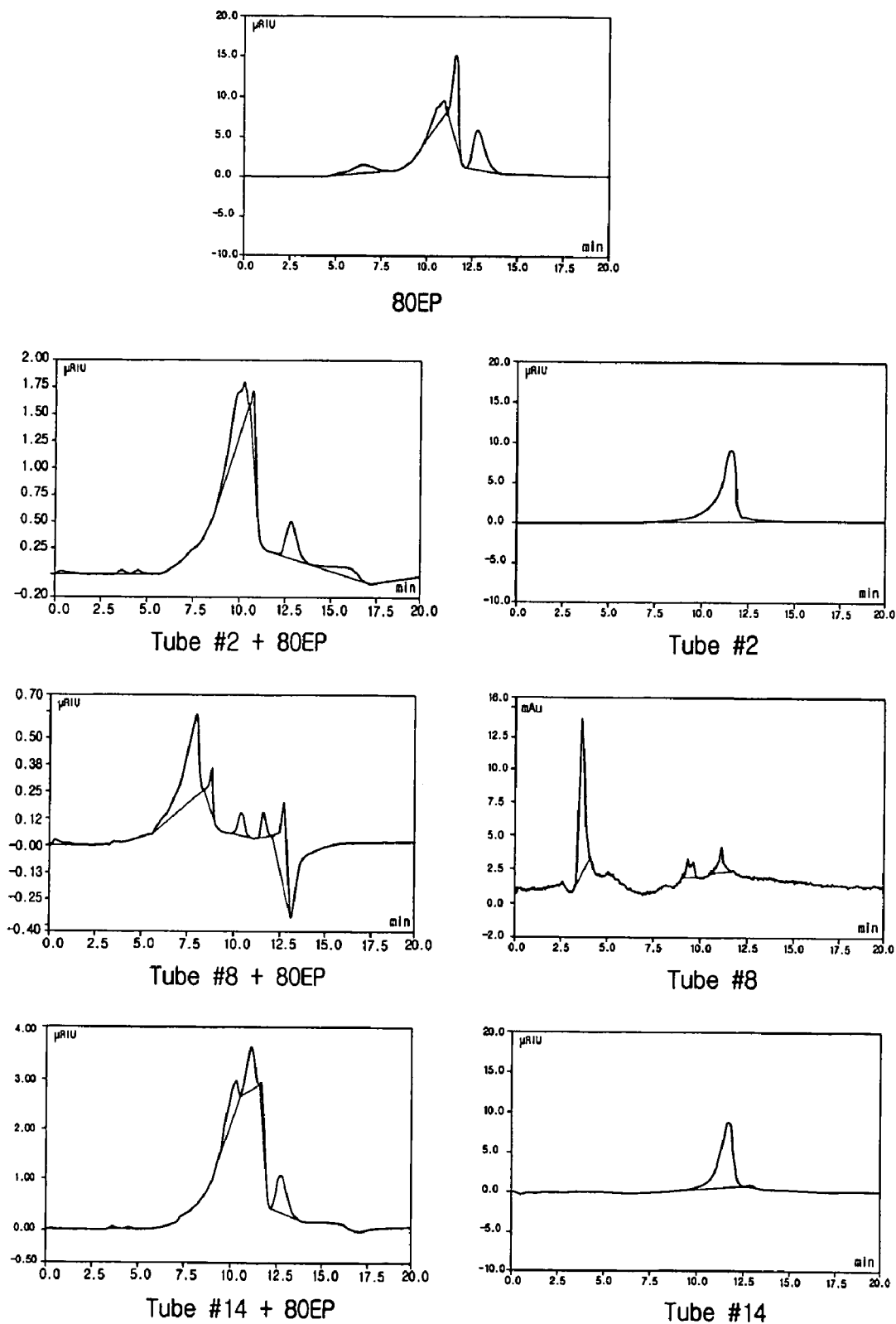
FIGS. 7a and 7b are HPLC chromatograms of each fraction containing autolysis enzyme separated from HPLC (TSK column) before and after being treated with 80 EP.
Figure 7B:
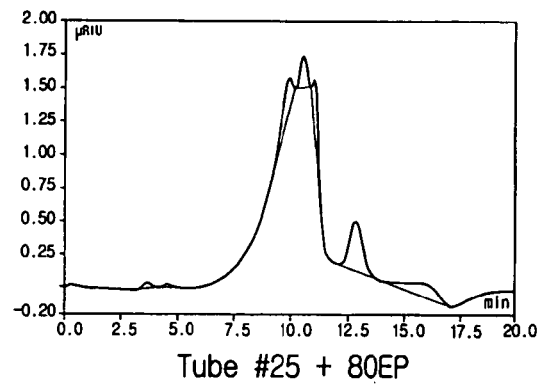
Figure 7B:
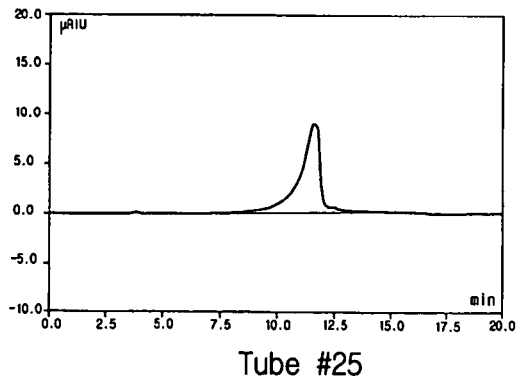
Figure 7B:
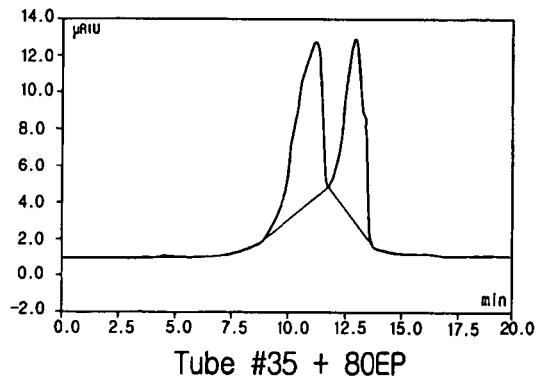
Figure 7B:
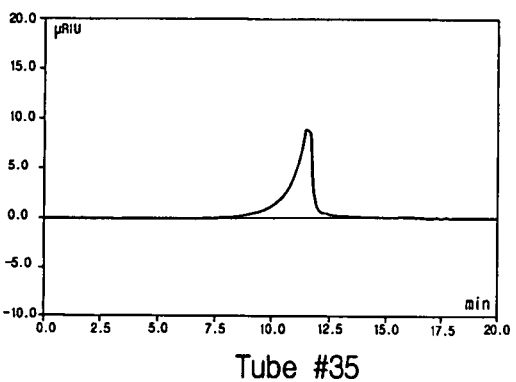
Figure 7B:
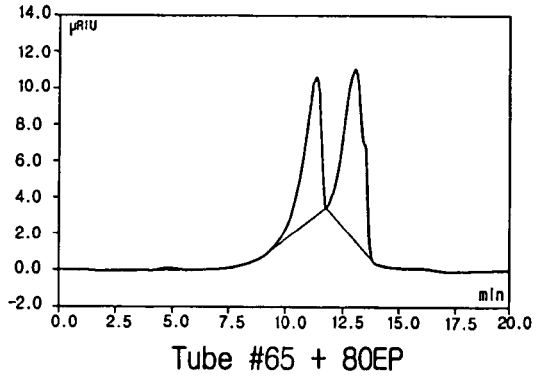
Figure 7B:
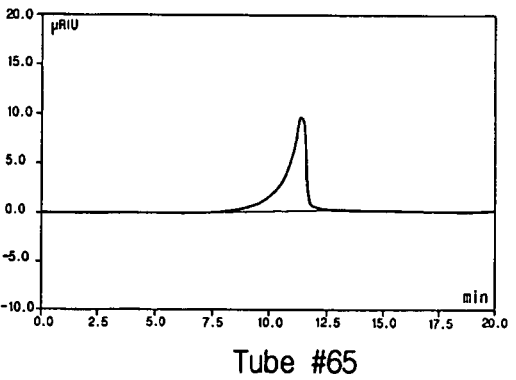
Figure 7B:
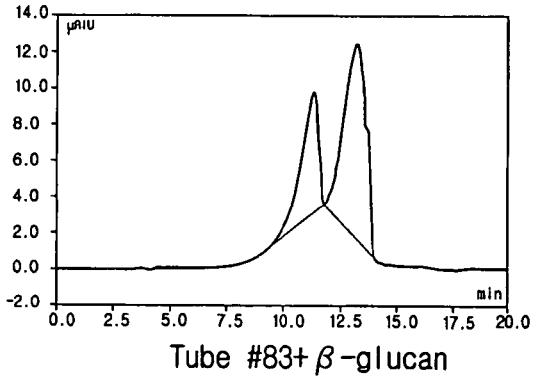
Figure 7B:
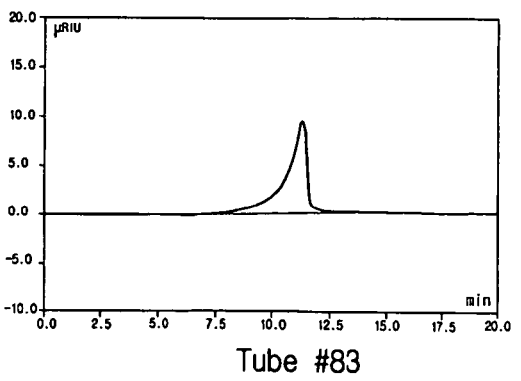

FIGS. 7a and 7b are HPLC chromatograms of each fraction containing autolysis enzyme separated from HPLC (TSK column) before and after treating with 80 EP. The horizontal axis represents time (minutes) and the vertical axis represents length (mAU). The left panel shows HPLC chromatograms of each fraction of #2, #8, #14, #25, #35, #65 and #83 treated with 80 EP and the right panel shows HPLC chromatograms of each fraction.

As shown in FIGS. 7a and 7b, the uppermost chromatogram of 80 EP has four peaks. When each fraction of autolysis enzyme separated from DEAE chromatography (FIG. 3) was reacted with 80 EP, the fraction of tube #8 showed different pattern from that of 80 EP, which represents that new product has been formed. In the other fractions, however, the original pattern of 80 EP was maintained, which means that digestion has not been carried out. Accordingly, it is considered that the high molecular polysaccharides contained in 80 EP have been digested into medium or low molecular weight polysaccharides by the reaction with the fraction of tube #8.

Subsequently, the digest obtained from 80 EP treated with autolysis enzyme (tube #8) was separated with HPLC, and then monitored by UV detector and RI detector simultaneously.

Figure 8A:
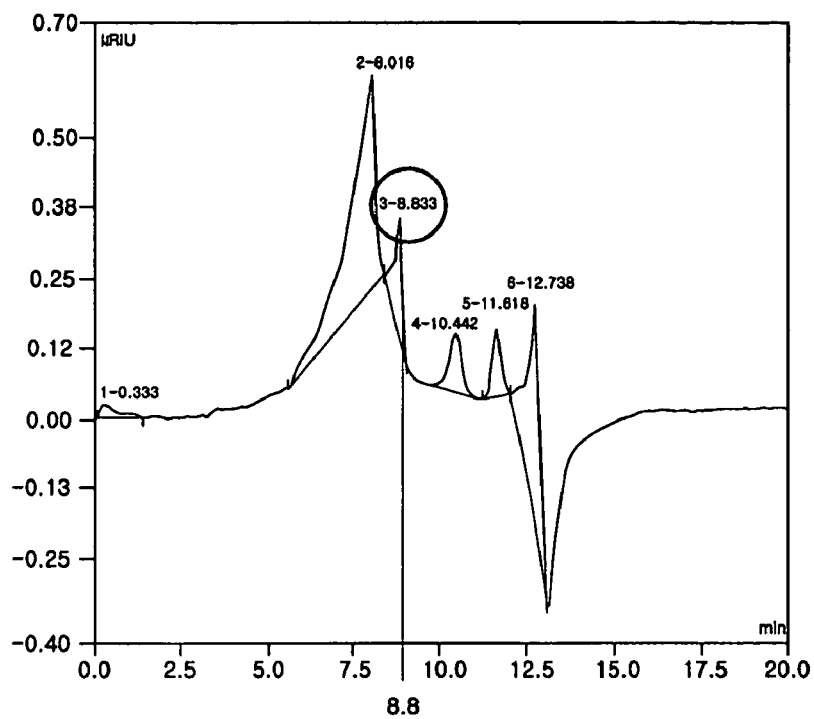
FIG. 8 is HPLC chromatograms of the products from 80EP treated with tube #8, which are detected with UV detector and RI detector.
Figure 8B:
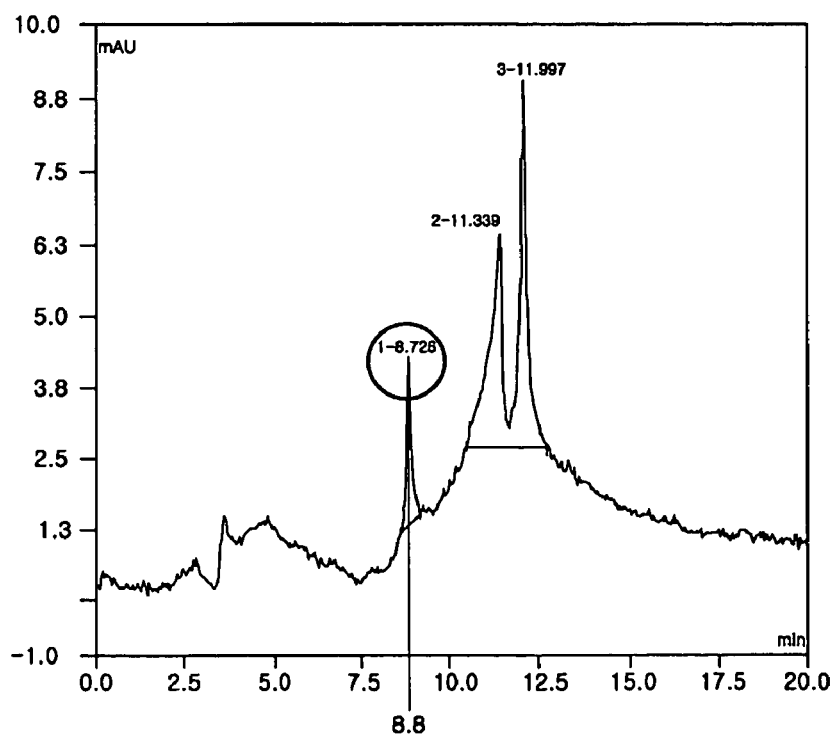

FIG. 8 are HPLC chromatograms of the products from 80EP treated with tube #8, which are detected with UV detector and RI detector. In FIG. 8, left panel A shows the result of RI detector and right panel B shows the result of UV detector (267 nm). As shown in FIG. 8, only RT 8.8 peak is detected by both UV detector and RI detector, and the other peaks are detected either UV detector or RI detector. Considering the pattern of RT 8.8 peak, it is confirmed that polysaccharides are coupled with another material (having UV absorbance) which is considered to be isoflavone having UV absorbance.

EXAMPLE 8

Confirmation of Production of Low and Medium Molecular Weight Isoflavone-β-D-Glucan by Autolysis Enzyme In order to confirm that low and medium molecular weight isoflavone-β-D-glucan was produced by autolysis enzyme during the liquid culture of AB mycelia, TLC was carried out.

When soybean powder (SP) was fractionated by ethanol (10, 20, 30, 40, 50, 60, 70 and 80%) and then each precipitate was separated, the most amount of precipitate was obtained in 70% ethanol, little amount was obtained in 10 to 60% ethanol, and small amount was obtained in 80% ethanol. Considering the most amount of precipitate derived from the liquid culture of AB mycelia has been obtained in 80 EP, it is considered that the precipitate contains such material that is not contained in SP but produced during the liquid culture of AB mycelia by bioconversion.

Figure 9:
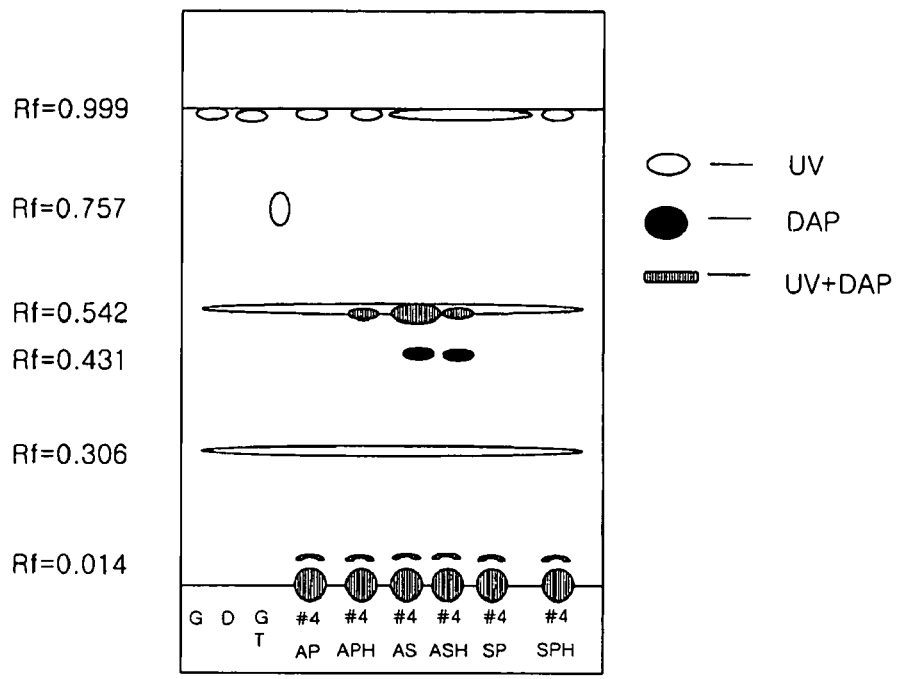
FIG. 9 shows TLC pattern of soybean powder and its acid hydrolyzate.

FIG. 9 shows TLC pattern of soybean powder (SP) and its acid hydrolyzate (SPH). In FIG. 9, AP means precipitate of 80 EP obtained from the liquid culture of AB mycelia and then treated again with 80% ethanol; APH, acid-hydrolyzate of AP; AS, supernatant of the above 80 EP; ASH, hydrolyzate of AS; SP, soybean powder consisting of culture media; SPH, hydrolyzate of SP. G (genistein), D (daidzein) and GT (genistein standard) are markers and the vertical axis represents Rf values thereof.

As shown in FIG. 9, all the samples obtained from SP contain the materials having UV absorbance (RF 0.999, 0.542, 0.306) alone (especially, G and D, etc.) and do not contain the materials detected in UV lamp and DAP simultaneously, which shows that SP provides the materials having UV absorbance alone. On the other hand, the fraction obtained from AP has the material detected in UV and DAP simultaneously (Rf 0.542, 0.014), which means that the material is not contained in culture medium but produced during the liquid culture of AB mycelia by bioconversion.

Figure 10:
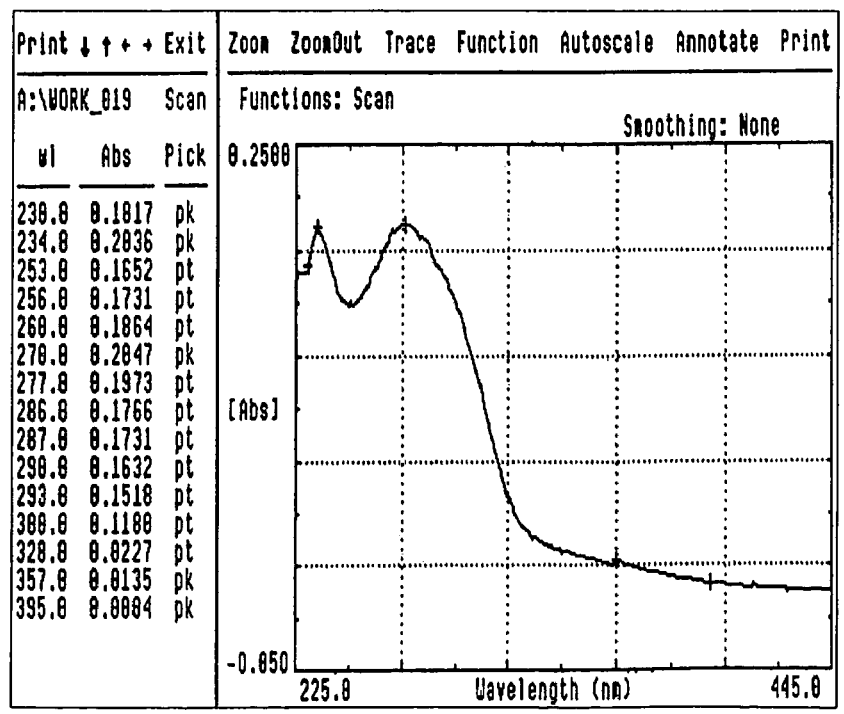
FIG. 10 is UV/VIS spectra of autolysis enzyme-treated 80EP.
Figure 11A:
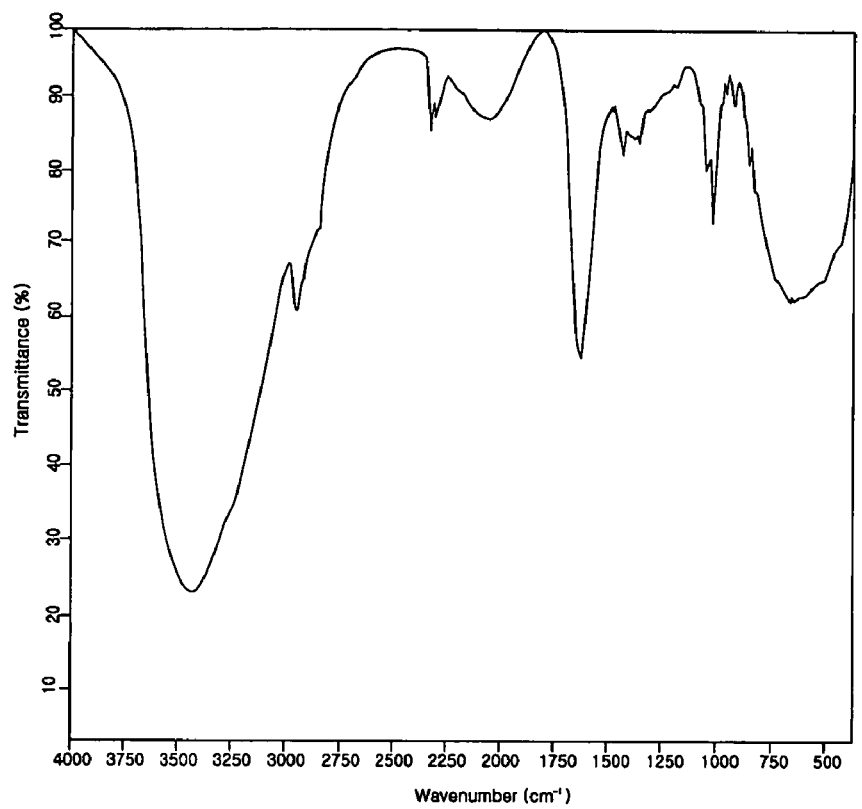
FIGS. 11a, 11b and 11c are IR spectra of TLC bands of FIG. 9.
Figure 11B:
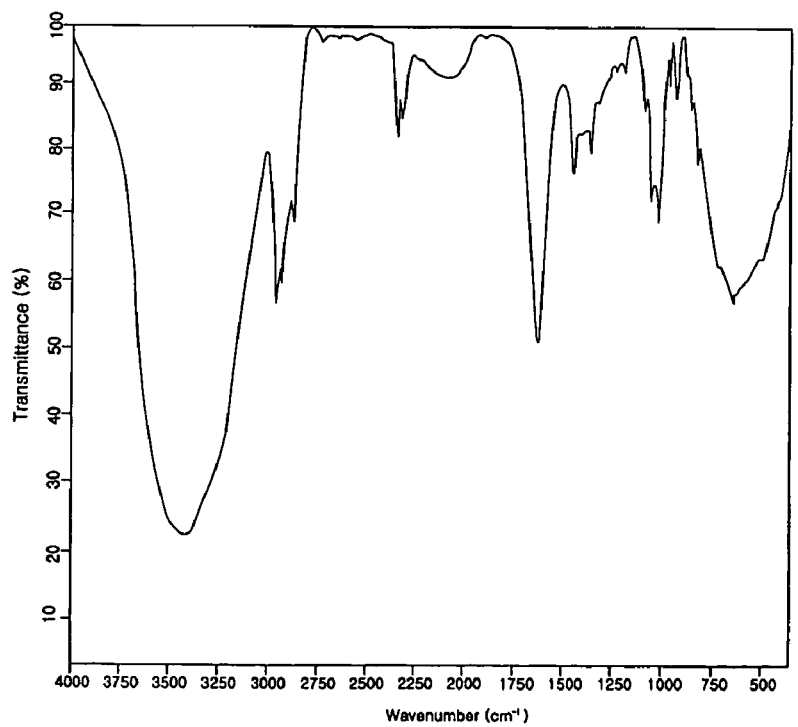
Figure 11C:
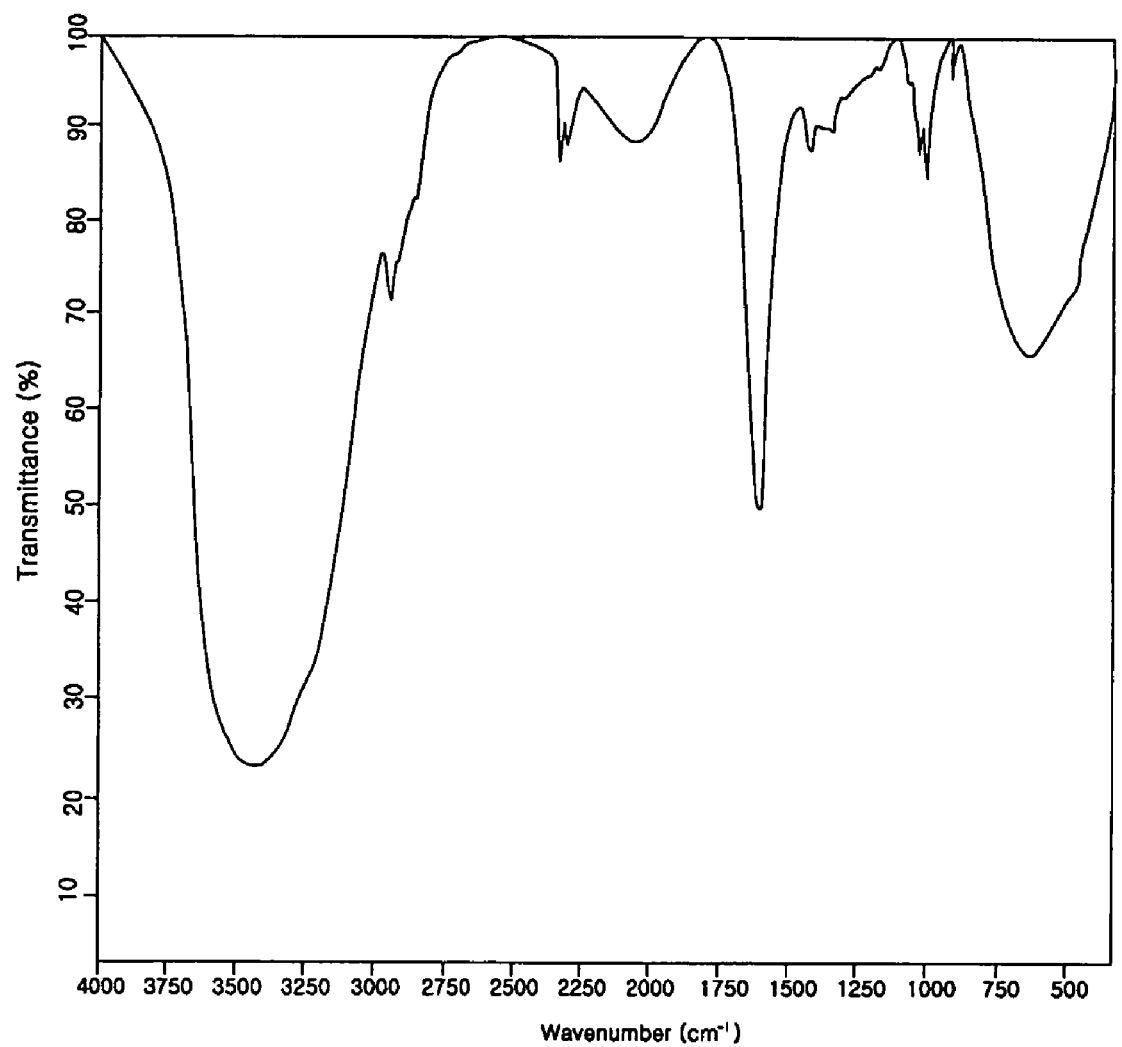

FIG. 10 is UV/VIS spectra of autolysis enzyme-treated 80EP and FIGS. 11a, 11b and 11c are IR spectra of TLC bands of FIG. 9. As shown in FIGS. 10, 11a, 11b and 11c, all the spectra are similar to those of G and D, which means that they are glycosides of G or D. It is considered that the materials are produced during the liquid culture by bioconversion.

According to the above Examples 7 and 8, it is confirmed that high molecular weight β-D-glucan is digested to low and medium molecular weight β-D-glucan by autolysis enzyme, and the product is not made exclusively of low and medium molecular weight β-D-glucan but formed in combination with a certain material which is not polysaccharide.

EXAMPLE 9

Identification of Isoflavone Contained in Final Product

Isoflavone-β-D-glucan which is finally separated and purified according to the present invention (A) and isoflavone-β-D-glucan hydrolyzed by enzyme (β-glucosidase and megazyme kit) (B) were analyzed by HPLC (C18 column, mobile phase; MeOH: 1 mM ammonium acetate (6:4), flow rate; 1 ml/min).

Table 3 shows the content of free genistein and daidzein in A and B.

TABLE 3

|  | Genistein | Daidzein |
|---|---|---|
| isoflavone-β-D-glucan (A) | — | — |
| isoflavone-β-D-glucan hydrolyzate (B) | 150 mg/g dry weight | 28.2 mg/g dry weight |

As shown in Table 3, no free genistein and daidzein was detected in A and 150 mg/g dry weight of genistein and 28.2 mg/g dry weight of daidzein were detected in B. The result means that the final product of the present invention does not contain genistein and daidzein, free form of isoflavone, while the hydrolyzate of the final product contains them. Accordingly, it is considered that isoflavone is contained in the final product of the present invention (A), which contains isoflavone and β-D-glucan not as mixture but as glycoside.

EXAMPLE 10

Determination of Molecular Weight of Low and Medium Molecular Weight Isoflavone-β-D-Glucan Molecular weight of low and medium molecular weight isoflavone-β-D-glucan was determined by HPLC equipped with TSK column (PDA-100 UV detector and RI detector, P-680 pump, ASI-100 fraction collector, Dionex). Mobile phase was triple distilled water and flow rate was 1 ml/min.

Figure 13:
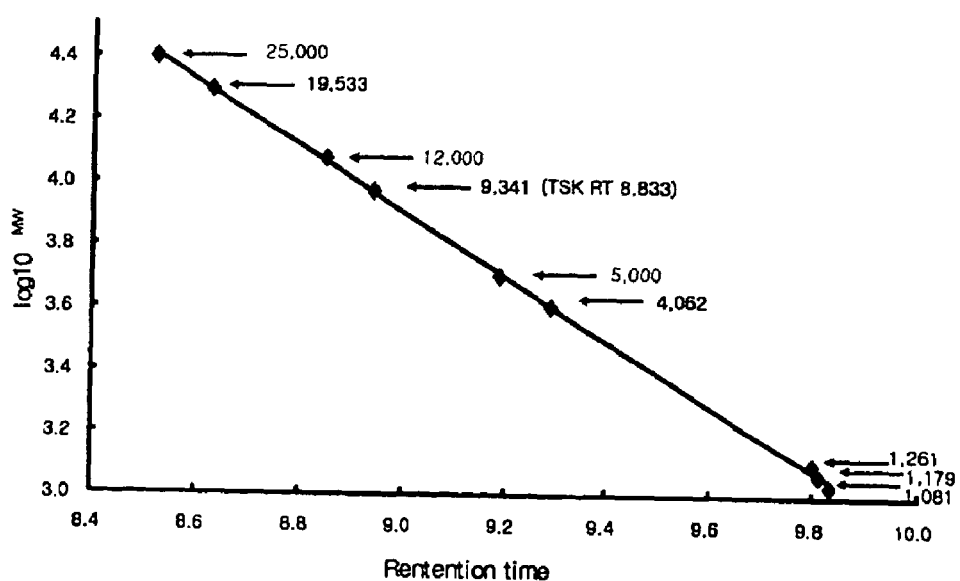
FIG. 13 is a graph showing molecular weight of low and medium molecular weight isoflavone-β-D-glucan according to the present invention calculated by comparing with dextran standard and displayed in log scale.

FIG. 13 is a graph showing molecular weight of low and medium molecular weight isoflavone-β-D-glucan according to the present invention calculated by comparing with dextran standard and displayed in log scale. As shown in FIG. 13, molecular weight of low and medium molecular weight isoflavone-β-D-glucan was about 25,000.

EXAMPLE 11

Structure of Low and Medium Molecular Weight Isoflavone-β-D-Glucan

Low and medium molecular weight isoflavone-β-D-glucan was separated again by HPLC (TSK column, mobile phase; $H_2O$) and then a fraction showing the greatest anticancer effect was collected. In the fraction, sugar and isoflavone (genistein, daidzein) was determined by IR, H-NMR and UV spectra.

Figure 14:
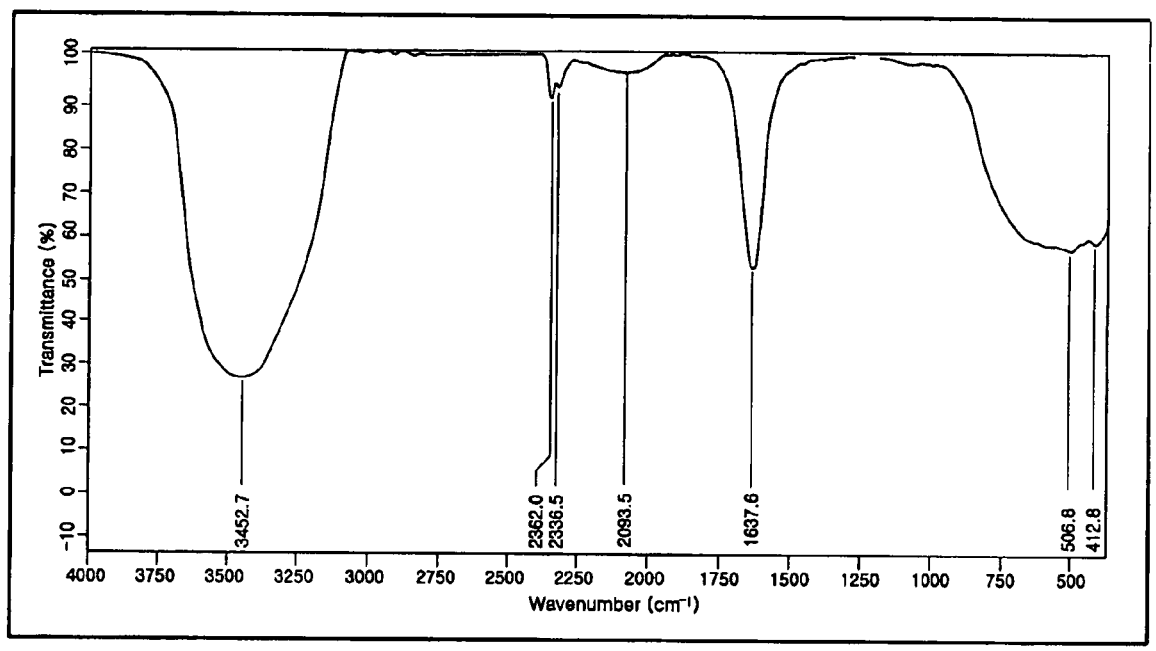
FIG. 14 is IR spectrum of low and medium molecular weight isoflavone-β-D-glucan according to the present invention.

FIG. 14 is IR spectrum of low and medium molecular weight isoflavone-β-D-glucan according to the present invention. In IR spectrum, the characteristic peaks were 495–656 $cm^{-1}$ (strong, broad), 1014 $cm^{-1}$ (strong, narrow), 1109 $cm^{-1}$ (weak, narrow), 1402.0, 1450.8, 1472.7 $cm^{-1}$ (weak, broad), 1642.6 $cm^{-1}$ (strong, narrow), 2097.0–2112.0 $cm^{-1}$ (medium weak, broad), 2390 $cm^{-1}$ (very weak, broad), 2843 $cm^{-1}$ (medium, narrow in OH absorbance~3000 $cm^{-1}$), 3173.0–3648 $cm^{-1}$ (broad in OH absorbance~3000 $cm^{31\ 1}$), the characteristic peaks shown in IR spectrum of G or D standard.

Figure 15:
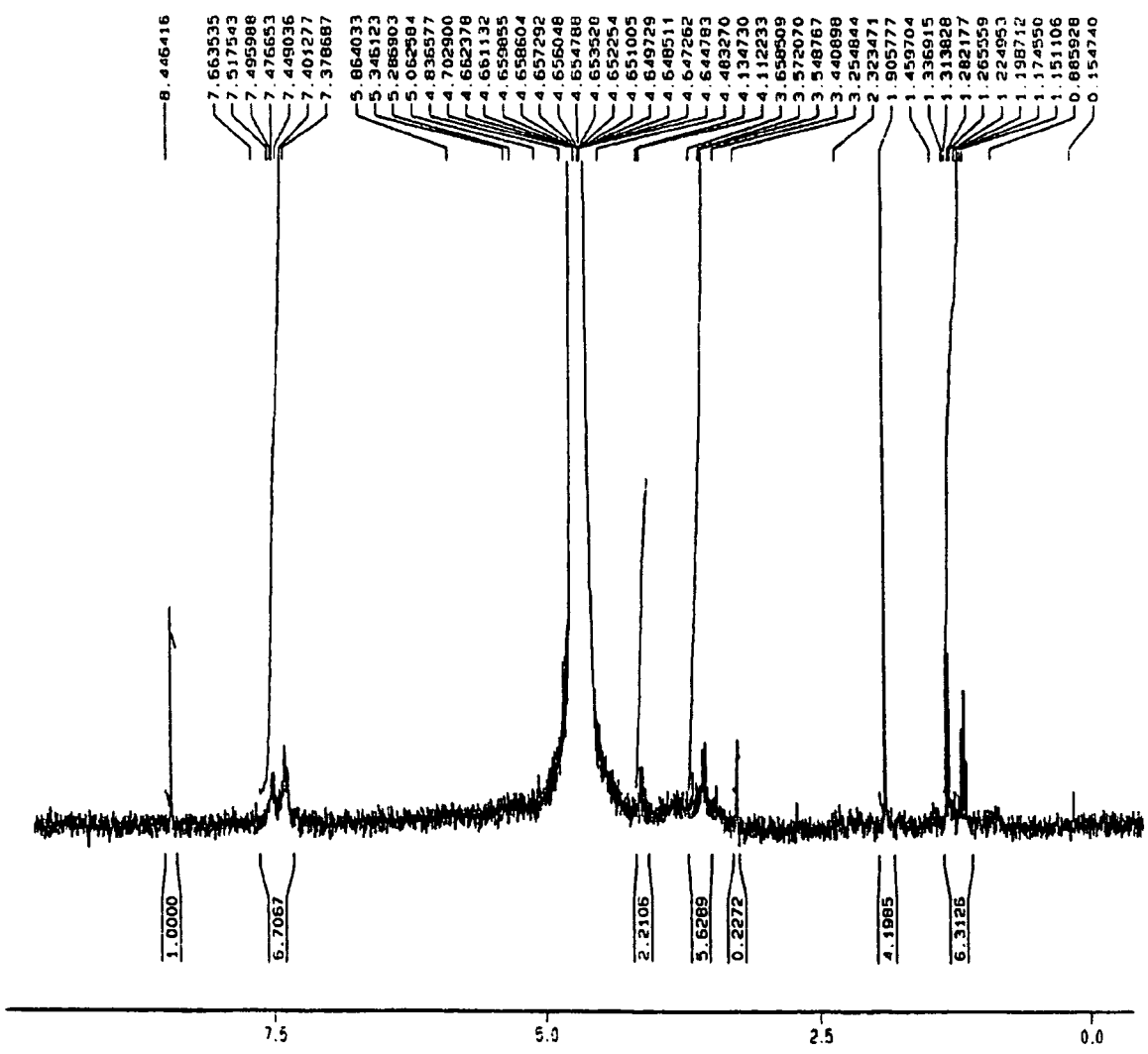
FIG. 15 is H-NMR spectrum of low and medium molecular weight isoflavone-β-D-glucan according to the present invention.
Figure 16:
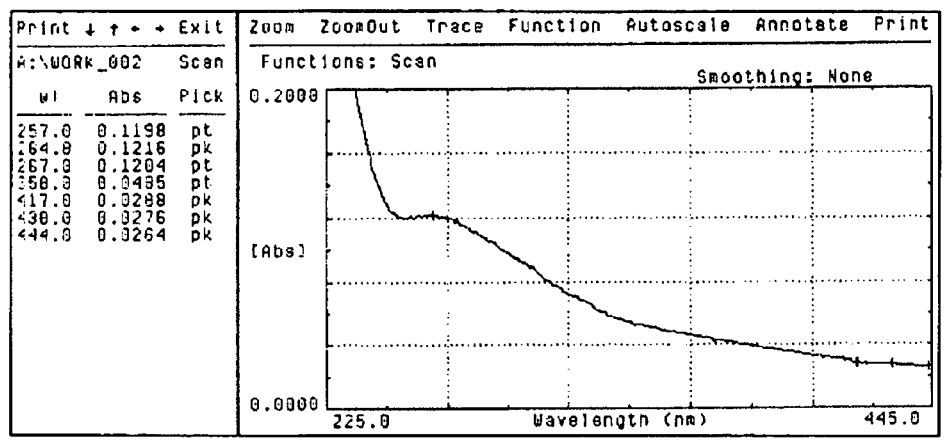
FIG. 16 is UV spectrum of low and medium molecular weight isoflavone-β-D-glucan according to the present invention.

FIG. 15 is H-NMR spectrum and FIG. 16 is UV spectrum of low and medium molecular weight isoflavone-β-D-glucan according to the present invention. As shown in FIG. 15, maximum absorbance was appeared in 267 nm, likewise that of G. Accordingly, it is considered that RT 8.8 peak indicates β-D-glucan containing mostly G among isoflavone.

EXAMPLE 12

Composition of Sugars

Sample was added with 5 ml of phosphate buffer (20 mM, pH 6.5) and then digested by megazyme kit (β-glucosidase; 0.2 U, 0.1 ml) and licenase (10 U, 0.2 ml). The digest was analyzed by HPLC (Rezo RCM-monosaccharide column, 200×10 mm) to identify the composition of sugars.

Figure 17:
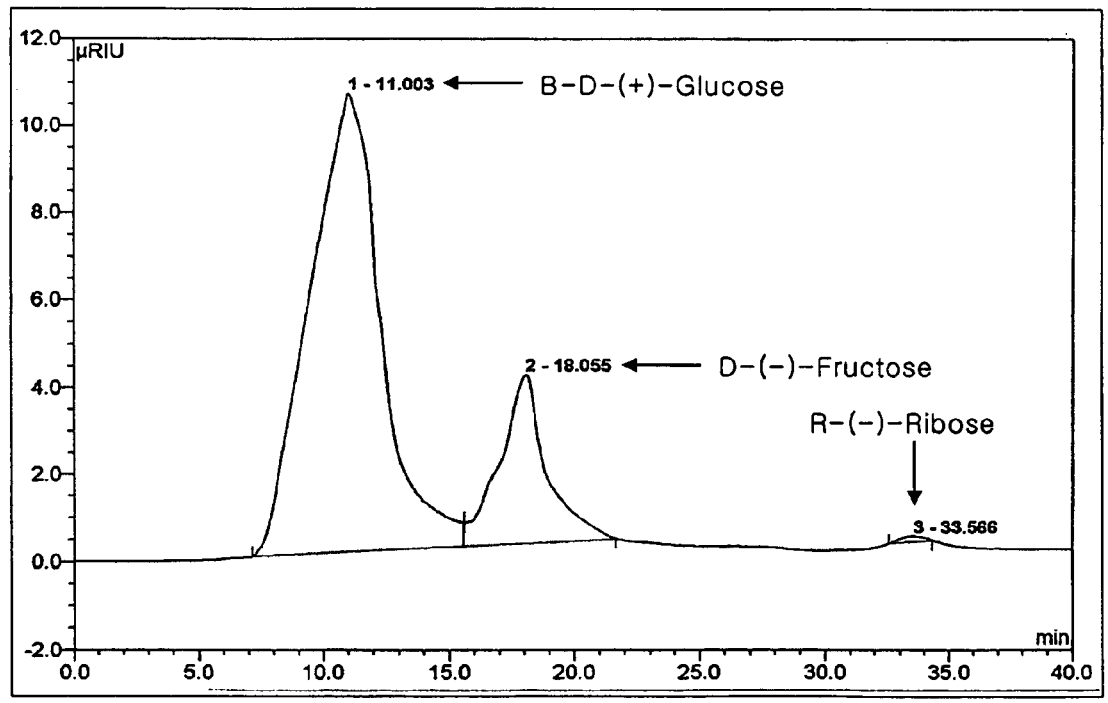
FIG. 17 shows the composition of monosaccharide of low and medium molecular weight isoflavone-β-D-glucan according to the present invention.

FIG. 17 shows the composition of monosaccharide of low and medium molecular weight isoflavone-β-D-glucan according to the present invention (RT 8.8). As shown in FIG. 17, the low and medium molecular weight isoflavone-β-D-glucan according to the present invention (RT 8.8) includes β-D-glucose, D-fructose and ribose.

Preparation Example 1

Production of High Molecular Weight Isoflavone-β-D-Glucan (MW 30,000 or More) by Culturing AB Mycelia in Liquid Medium Containing Isoflavone 40 g of soybean or soybean powder was added with 10 g of protease and 10 g of cellulase and then digested at 60° C. and 200 rpm for 1 to 5 hours. The digest may be used with or without addition of 10 to 1000 mg of natural isoflavone separated from vegetables or synthetic isoflavone. 220 g of brown sugar, 3 g of ribose and inorganic salts (10 g of $MgSO_4$, 10 g of $KH_2PO_4$) were added thereto and then water was added to make the total volume 1 l. The mixture was autoclaved at 121° C. for 1 hour to make liquid culture medium.

*Agaricus blazei* mycelia were inoculated into the liquid medium, and then cultured upon shaking or aeration at 25~35° C. for 1~7 days.

Preparation Example 2

Separation of High Molecular Weight Isoflavone-β-D-Glucan

The culture obtained in Preparation Example 1 was autoclaved at 121° C. for 1 hour, filtrated through diatomite, and then concentrated to ⅒ volume under vacuum. 200 g of the concentrate was added with ethanol to be 80% ethanol solution and then mixed. The mixture was placed at 4° C. for 24 hours to induce precipitation. The precipitated liquid was centrifuged at 10,000 rpm for 10 minutes and the supernatant was removed to obtain 3.8 g of the precipitate containing β-D-glucan having the molecular weight of 100,000 or more (80 EP).

Preparation Example 3

Separation and Purification of Autolysis Enzyme from Liquid Culture of *Agaricus blazei* mycelia Liquid culture of AB mycelia was filtrated under reduced pressure and the filtrate was mixed with TCA to make 10% TCA solution. The mixture was placed at 4° C. for 24 hours and then centrifuged at 4° C. and 10,000 rpm for 15 minutes to separate the precipitate.

The precipitate was dissolved in 50 mM sodium acetate buffer (pH 5.0) and then separated by DEAE column (2 cm, 110 cm) to collect factions by 10 ml. The mobile phase was 20 mM sodium phosphate buffer (20 mM $NaH_2PO_4$ and 20 mM $Na_2HPO_4$, pH 7.0).

Preparation Example 4

Production of Low and Medium Molecular Weight Isoflavone-β-D-Glucan

After adjusting the pH to 5.5, 80 EP obtained in Preparation Example 2 was added with 10 ml of autolysis enzyme separated from DEAE column, and then the mixture was incubated in shaking incubator at 53° C. for 1 hour.

The production of low and medium molecular weight isoflavone-β-D-glucan (MW 30,000 or less) by autolysis enzyme was confirmed by TLC and HPLC as mentioned above.

Preparation Example 5

Separation and Purification of Low and Medium Molecular Weight Isoflavone-β-D-Glucan (1) DEAE Column Chromatography 3 ml of the autolyzed product obtained in Preparation Example 4 was loaded on DEAE column (2 cm, 110 cm) filled with 5 mM sodium phosphate buffer (pH 7.7) and every 310 drops (10 ml) fractions were collected. The mobile phase was 5 mM sodium phosphate buffer (5 mM $NaH_2PO_4$ and 5 mM $Na_2HPO_4$, pH 7.7).

(2) Silica Gel Column Chromatography

The fraction obtained by DEAE column chromatography was concentrated by vacuum concentrator and separated again by silica gel column chromatography. The mobile phase was butanol:ethanol:$H_2O$ (5:3:3).

Low and medium molecular weight isoflavone-β-D-glucan in the separated fraction was confirmed by TLC and HPLC as mentioned above.

Hereinafter, the anti-cancer effect and immunoenhancing effect of low and medium molecular weight isoflavone-β-D-glucan as produced above will be described in detail, in conjunction with various examples.

Experiment 1

Cytotoxicity against S-180 Ascites Cancer Cells

S-180 cells were maintained and subcultured at 37° C. in a humidified $CO_2$ incubator (95% air-5% $CO_2$). The complete medium for cell maintenance consisted of DMEM (Dulbecco's modified Eagle's medium) containing 10% horse serum, 100 U/ml penicillin and 100 μl/ml streptomycin. When cells were 80% confluent, the medium was changed every two days.

10 mg/ml of sample in double distilled water (DDW) was diluted by 10 fold in DMEM to make a sample solution containing 100 μl of DDW and 900 μl of DMEM, while control solution contained 100 μl of DDW and 900 μl of DMEM. $1.5 \times 10^5$ cells/ml of S-180 cells were diluted with DMEM to be $5 \times 10^4$ cells/ml of DMEM.

To measure the effect of 80 EP on cell growth curves, cells were plated in complete medium in 24-well plates. All wells were treated with $5 \times 10^4$ cells/ml DMEM and then with each sample or control. The treated well plates were cultured in 5% $CO_2$ incubator at 37° C. for 48 hours. Alive cells were dyed by 0.2% tryphane blue and the number of viable cells was determined by counting in a hemocytometer to calculate $ED_{50}$.

Table 4 shows the toxicity of the sample from 80 EP fraction treated with autolysis enzyme (tube #8) against S-180 cancer cells. As shown in Table 4, the cell number of control was $23.7 \times 10^4$ cells/ml after 48 hours of incubation. The cell numbers treated with autolyzed AB in each concentration of 10, 20 and 30 μg/ml were $7.5 \times 10^4$, $6.0 \times 10^4$ and $5.5 \times 10^4$ cells/ml, respectively, resulting in 0.9 μg/ml of $ED_{50}$. On the other hand, the cell numbers treated with AB without autolysis in each concentration of 10, 20 and 30 μg/ml were $11.0 \times 10^4$, $9.5 \times 10^4$ and $8.5 \times 10^4$ cells/ml, respectively, resulting in 2.1 μg/ml of $ED_{50}$. The result shows that the cytotoxicity increases in the sample treated with autolysis enzyme. Accordingly, it is considered that cytotoxic substances are generated from 80 EP fraction by the treatment of autolysis enzyme.

TABLE 4

| Treatment | Doses (μg/ml) | Growth of Cells ($\times 10^4$ cells/ml) | Growth Ratio (%) | $ED_{50}$ (μg/ml) |
|---|---|---|---|---|
| Control | 10 | 23.7 ± 2.5 | 100 | — |
|  | 20 |  |  |  |
|  | 30 |  |  |  |
| AB | 10 | 11.0 ± 0.7 | 31.11 | 2.1 |
|  | 20 | 9.5 ± 1.4 | 23.32 |  |
|  | 30 | 8.5 ± 0.7 | 18.14 |  |
| Autolyzed AB | 10 | 7.5 ± 0.7 | 12.95 | 0.9 |
|  | 20 | 6.0 ± 0.1 | 5.18 |  |
|  | 30 | 5.5 ± 1.4 | 2.59 |  |

Experiment 2

Anticarcinogenicity Against Mouse Ascite Cancer 7 week-old female ICR (Institute for Cancer Research) mice were obtained from Life Science (Taegu, Korea). S-180 cells were supplied by Korean Cell Line Bank (Seoul, Korea). The culture medium for S-180 was obtained by GIBCO and other reagents used were first grade.

The ICR mice were grouped by 10 mice so that each group had equal mean body weight and then each group was put into a cage. The mice were raised freely with food and water for 1 week in an animal house at controlled room temperature and relative humidity. S-180 cells were subcultured as ascites type in ICR mice, and the tumor cells were harvested from the abdominal cavities of the mice 7 days after the implantation. 0.1 ml of S-1 80 cells ($1 \times 10^7$ cells/ml PBS) was transplanted subcutaneously into the abdomen of each mice to induce ascite cancer. 0.1 ml of test sample, dissolved or suspended in PBS (0.01M, pH 7.0) in adequate concentrations, was injected intraperitoneally every two days for 2 weeks, starting 24 hours after tumor implantation. After the intraperitoneal injection of S-180, the weight of mouse and the amount of feed intake were measured every three days for 40 days. The number of survived mice and the number of survival days were also measured.

Table 5 shows the number of survived mice and survival days of control group, the group treated with 80 EP, and the group treated with autolyzed 80 EP. As shown in Table 5, the average survival days of control group was 19.2 days, while it was extended to 26.9 days (lengthen the life span by 40%) by the treatment of autolyzed AB and 3 mice were still alive after 40 days. The treatment of AB also lengthened survival days compared with control but less effective than autolyzed AB.

TABLE 5

| Treatment | Mean survival days | Survival rate (%) | Survived mice |
|---|---|---|---|
| Control | 19.2 | 100 | 0/10 |
| AB | 22.3 | 116 | 0/10 |
| Autolyzed AB | 26.9 | 140 | 3/10 |

Experiment 3

Cytotoxicity Against Human Cancer Cell Lines (1) Medium: 1 pack of DMEM was dissolved in 900 ml of triple distilled water and then added with 1 ml of penicillin-streptomycin. The mixture was added with 2 g of sodium bicarbonate and 100 ml of FBS (fetal bovine serum), and then filtrated by filter paper (0.22 μm). The complete medium for cell maintenance was stored at 4° C.

(2) Cell culture: Human cancer cell lines (MCF-7, breast cancer and Hela, uterine cervix cancer cell) were subcultured in DMEM medium at 37° C. for 24 hours in 5% $CO_2$ incubator. The cultured cell lines were treated with 1 ml of trypsin-EDTA at 37° C. for 10 minutes so that cells were separated from medium. Cells were recovered by centrifugation (1,500 rpm, 2 minutes) and then dissolved in the above medium. 1 ml of the medium containing cells was distributed in 12 well-plates so that each well contained $5 \times 10^4$ cells.

(3) Cytotoxicity Against Hela Cell and MCF-7 Cell

Table 6 shows the cytotoxicity of the samples from 80 EP fraction treated with or without autolysis enzyme (tube #8) against Hela cell (uterine cervix cancer cell line). As shown in Table 6, the cell number of Hela cells was $20.1 \times 10^4$ cells/ml after 48 hours incubation. $ED_{50}$ values of AB and autolyzed AB were 5.6 and 0.9 ρg/ml, respectively. Accordingly, it is considered that autolyzed AB has strong cytotoxicity and cytotoxic substances are produced from 80 EP fraction by the treatment of autolysis enzyme.

TABLE 6

| Treatment | Doses (μg/ml) | Growth of Cells ($\times 10^4$ cells/ml) | Growth Ratio (%) | $ED_{50}$ (μg/ml) |
|---|---|---|---|---|
| Control | 10 | 20.1 ± 1.1 | 100 | — |
|  | 20 |  |  |  |
|  | 30 |  |  |  |
| AB | 10 | 11.0 ± 1.4 | 36.4 | 5.6 |
|  | 20 | 9.5 ± 1.4 | 27.2 |  |
|  | 30 | 7.0 ± 0.7 | 12.1 |  |
| Autolyzed AB | 10 | 7.0 ± 0.7 | 18.1 | 0.9 |
|  | 20 | 6.0 ± 0.1 | 15.1 |  |
|  | 30 | 5.5 ± 1.4 | 3.0 |  |

Table 7 shows the cytotoxicity of the samples from 80 EP fraction treated with or without autolysis enzyme (tube #8) against MCF-7 cell (breast cancer cell line). As shown in Table 7, the cell number of MCF-7 cells was $21.5 \times 10^4$ cells/ml after 48 hours incubation. $ED_{50}$ values of AB and autolyzed AB were 5.8 and 1.2 μg/ml, respectively, which were similar to those for Hela cells.

TABLE 7

| Treatment | Doses (μg/ml) | Growth of Cells ($\times 10^4$ cells/ml) | Growth Ratio (%) | $ED_{50}$ (μg/ml) |
|---|---|---|---|---|
| Control | 10 | 21.5 ± 2.1 | 100 | — |
|  | 20 |  |  |  |
|  | 30 |  |  |  |
| AB | 10 | 12.0 ± 1.4 | 39.3 | 5.8 |
|  | 20 | 9.5 ± 1.4 | 27.2 |  |
|  | 30 | 80 ± 1.4 | 18.1 |  |
| Autolyzed AB | 10 | 8.5 ± 0.7 | 21.2 |  |
|  | 20 | 7.0 ± 0.1 | 18.1 | 1.2 |
|  | 30 | 5.5 ± 1.4 | 6.1 |  |

(4) Cytotoxicity Against Caxo-2 Cells

80 EP fraction treated with autolysis enzyme (tube #8 or fractionated by HPLC as FIG. 5) was fractionated by DEAE cellulose column chromatography to collect 6 fractions (tube #4, #14, #25, #32, #68 and #83).

Figure 18:
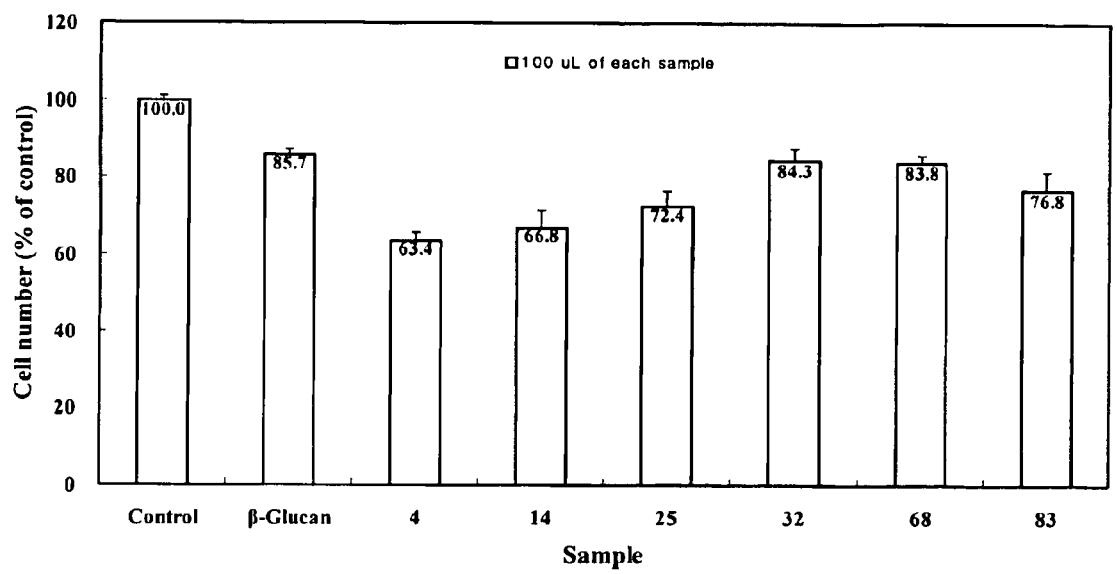
FIG. 18 shows the cytotoxic effects of the products of 80EP treated with autolysis enzyme on human colon cancer Caco-2 cells.

FIG. 18 shows the cytotoxic effects of the products of 80EP treated with autolysis enzyme on human colon cancer Caco-2 cells. In FIG. 18, the height of bar represents percentage of cell number after the treatment of autolysis enzyme as compared with control. As shown in FIG. 18, 80 EP fraction without treatment of autolysis enzyme shows 85.7% of viability, that is, 14% of cytotoxicity. On the other hand, tube #4 and #14 treated with autolysis enzyme show 37% and 33% of cytotoxicity, respectively. Other samples also show toxicity at a lesser extent. These result also suggest that cytotoxic substances are produced from 80 EP fraction by the treatment of autolysis enzyme.

Figure 19:
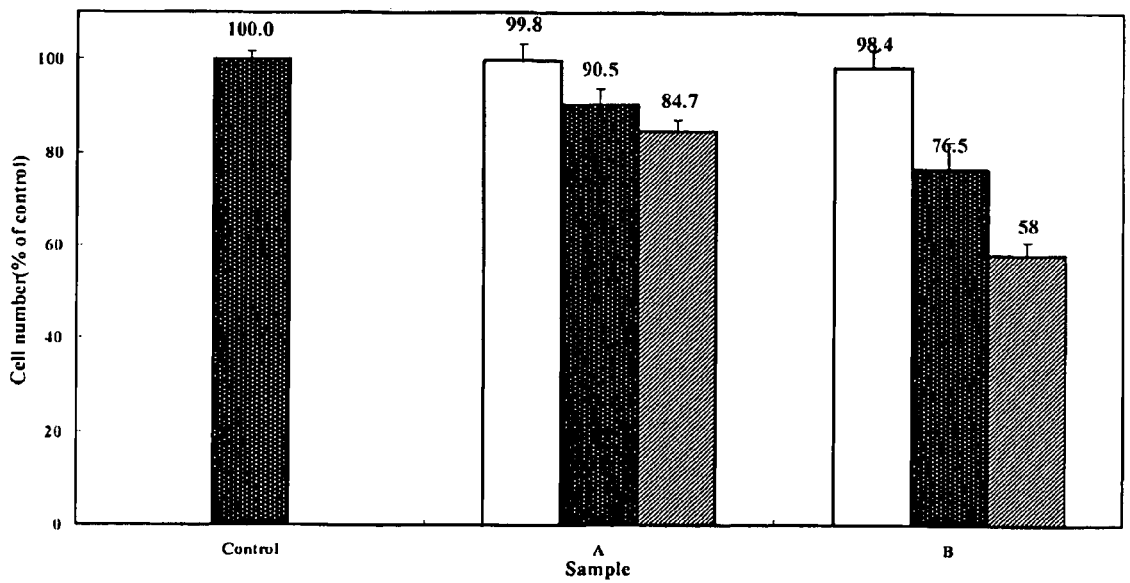
FIG. 19 shows the comparison of cytotoxicity of 80EP treated with tube #8 with various concentrations.

FIG. 19 shows the comparison of cytotoxicity of 80EP treated with tube #8 with various concentrations. In FIG. 19, sample A is 80 EP without treatment of autolysis enzyme and sample B is 80 EP treated with autolysis enzyme. The height of bar represents percentage of cell number after the treatment of autolysis enzyme as compared with control, in which concentration of white bar, dotted bar and shaded bar are 1, 5 and 10 mg, respectively. In sample A, cytotoxicity was not affected by the increase of concentration, while in sample B, cytotoxicity increased to 2, 23 and 42%, respectively, with the treatment of autolysis enzyme by 1, 5 and 10 mg. These result also suggests that cytotoxic substances are produced from 80 EP fraction by the treatment of autolysis enzyme.

Experiment 4

Immunoenhancing Effect of Isoflavone-β-D-Glucan

Female ICR mice (6~7 weeks of age) were housed in polycarbonated cage (4 mice/cage) and raised with feeding pellet fodder for mouse for 1 weeks and those of 28±1 g body weight were selected for experiment. All mice were raised freely with food and water in an animal house at 22±1° C. room temperature and 50% relative humidity maintaining light-and-dark cycle of 12 hour interval.

One week later, the mice were subjected to one of the following treatments for 14 days: 0 (control), 1, 2 and 4 mg/g body weight/0.2 ml distilled water. Samples were injected per os. At the end of 14 consecutive feeding days, mice were weighted and injected intraperitoneally with 1 mg/kg body weight of lipopolysaccharide (LPS, Sigma Chemical Co.) in sterile HEPES buffer (Sigma Chemical Co.) or HEPES buffer alone. All mice were weighted 4, 8, 12, 24, 48 and 72 hours post injection.

Figure 20:
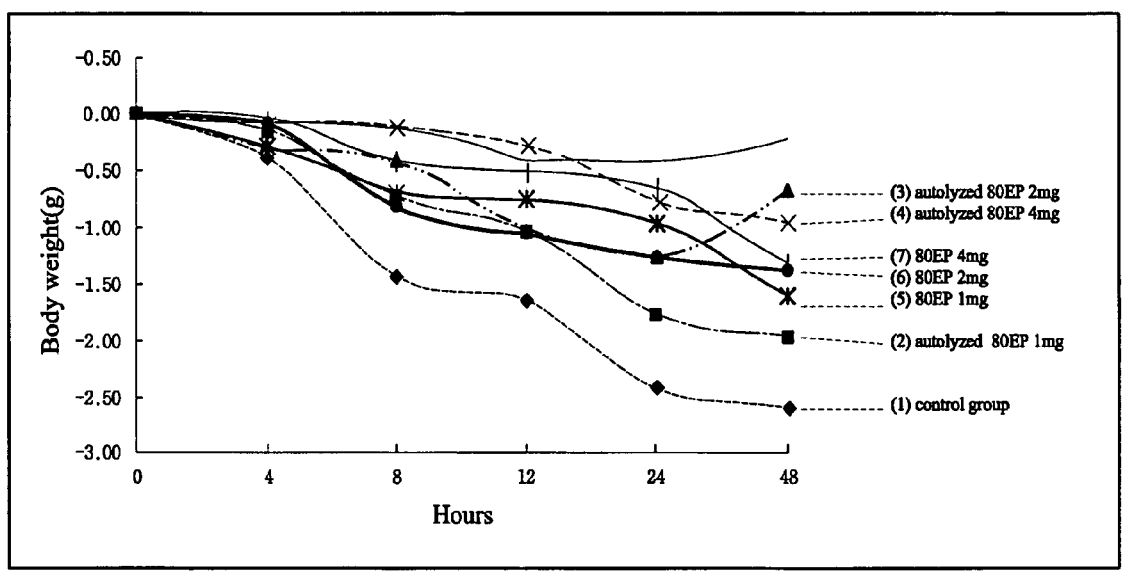
FIG. 20 shows the effect of 80EP treated with autolysis enzyme on the reduction of ICR female mouse body weight induced by lipopolysaccharide (LPS).

FIG. 20 shows the effect of 80EP treated with autolysis enzyme on the reduction of ICR female mouse body weight induced by lipopolysaccharide (LPD). In FIG. 20, (1) represents control group; (2), (3) and (4) represent the groups treated with 1, 2 and 4 mg of autolyzed 80 EP, respectively; and (5), (6) and (7) represent the groups treated with 1, 2 and 4 mg of 80 EP without treatment of autolysis enzyme.

LPS, a complex of lipid and polysaccharide with a covalent bond, forms an endotoxin consisting in outer membrane component of Gram negative bacteria. LPS has various biological activity and is called endotoxin. LPS of bacteria is recognized as the signal of infection by the immune system of host. Accordingly, immune ability may be presumed by determining the reduction of body weight after the treatment of LPS.

As shown in FIG. 20, all mice treated with LPS showed reduction of body weight. In control mice treated with LPS, body weight decreased dramatically with the lapse of time and resulted in 2.42 g reduction in 24 hours after the treatment of LPS. The treatment of 80 EP treated with autolysis enzyme (autolyzed AB) suppressed the reduction of body weight as compared with that of control. In autolyzed AB groups, the reductions of body weight in 24 hours after the treatment of LPS were −1.77, −1.22 and −0.75 g, respectively, with the treatment of 1, 2 and 4 mg of autolyzed AB. Accordingly, it is considered that autolyzed AB may reduce the effect of LPS. The AB sample (80 EP without treatment of autolyzed enzyme) was less effective for the suppression of body weight reduction, compared to autolyzed AB sample. These results suggest that active substances which may suppress the effect of LPS in ICR mice are produced from 80 EP fraction by the treatment of autolysis enzyme, which means low and medium molecular weight isoflavone-β-D-glucan has immunoenhancing effect.

INDUSTRIAL APPLICABILITY

The present invention provides low and medium molecular weight isoflavone-β-D-glucan produced by submerged liquid culture of *Agaricus blazei*, a method of producing the isoflavone-β-D-glucan using autolysis enzyme of *Agaricus blazei* mycelia, and use of the isoflavone-β-D-glucan for anti-cancer and immunoenhancing effect.

According to the present invention, low and medium molecular weight isoflavone-β-D-glucan is prepared from high molecular weight isoflavone-β-D-glucan extracted from liquid culture of *Agaricus blazei* mycelia, by using autolysis enzyme secreted by *Agaricus blazei* mycelia at an optimum condition for the activity of the enzyme. The process requires a short period of time and enables the product to be obtained on a large scale at low cost.

Low and medium molecular weight isoflavone-β-D-glucan of the present invention has anti-cancer effect as well as immunoenhancing effect without toxic effect on normal cells. The anti-cancer effect is remarkably increased with immunoenhancing effect.

The invention claimed is:

1. A method of producing isoflavone-β-D-glucan, which comprises the steps of:
    a) culturing *Agaricus blazei* mycelia in a liquid medium containing isoflavone to produce an undigested isoflavone-β-D-glucan;
    b) separating the undigested isoflavone-β-D-glucan from the liquid culture of *Agaricus blazei* mycelia;
    c) separating an autolysis enzyme from a separate liquid culture of *Agaricus blazei* mycelia;
    d) adding the autolysis enzyme to the undigested isoflavone-β-D-glucan to produce a digested isoflavone-β-D-glucan having a molecular weight of 30,000 or less; and
    e) separating and purifying the digested isoflavone-β-D-glucan.

2. The method according to claim 1, wherein the step of separating the undigested isoflavone-β-D-glucan from the liquid culture of *Agaricus blazei* mycelia comprises:
    a) extracting the liquid culture of *Agaricus blazei* mycelia with boiling water and concentrating the extract;
    b) adding ethanol to the concentrated extract to form a precipitate; and
    c) separating the precipitate.

3. The method according to claim 2, wherein ethanol is added to a concentration of 80%.

4. The method according to claim 1, wherein the step of separating an autolysis enzyme from a separate liquid culture of *Agaricus blazei* mycelia comprises:
    a) filtrating the liquid culture of *Agaricus blazei* mycelia under reduced pressure;
    b) adding trichloroacetic acid to the filtered liquid culture of *Agaricus blazei* mycelia to form a precipitate; and
    c) separating the precipitate.

5. The method according to claim 1, wherein the autolysis enzyme is added to the undigested isoflavone-β-D-glucan at pH 4.5–5.5.

6. An isoflavone-β-D-glucan produced by a method comprising:
    a) culturing *Agaricus blazei* mycelia in a liquid medium containing isoflavone to produce an undigested isoflavone-β-D-glucan;
    b) separating the undigested isoflavone-β-D-glucan from the liquid culture of *Agaricus blazei* mycelia;
    c) separating an autolysis enzyme from a separate liquid culture of *Agaricus blazei* mycelia;
    d) adding the autolysis enzyme to the undigested isoflavone-β-D-glucan to produce a digested isoflavone-β-D-glucan having a molecular weight of 30,000 or less; and
    e) separating and purifying the digested isoflavone-β-D-glucan.

7. An anti-cancer agent comprising the isoflavone-β-D-glucan of claim 6.

* * * * *